(12) United States Patent
Crane et al.

(10) Patent No.: US 11,255,860 B2
(45) Date of Patent: Feb. 22, 2022

(54) GLUCOSE SENSOR

(71) Applicants: Baxter International Inc., Deerfield, IL (US); Baxter Healthcare SA, Glattpark (CH)

(72) Inventors: Barry Colin Crane, Oxfordshire (GB); William Paul Paterson, Oxfordshire (GB); Nicholas Paul Barwell, Oxfordshire (GB); Peter Edgley, Oxfordshire (GB)

(73) Assignees: Baxter International Inc., Deerfield, IL (US); Baxter Healthcare SA, Glattpark (CH)

( * ) Notice: Subject to any disclaimer, the term of this patent is extended or adjusted under 35 U.S.C. 154(b) by 194 days.

(21) Appl. No.: 15/881,489

(22) Filed: Jan. 26, 2018

(65) Prior Publication Data
US 2018/0306802 A1    Oct. 25, 2018

Related U.S. Application Data

(63) Continuation of application No. 13/686,760, filed on Nov. 27, 2012, now abandoned.
(Continued)

(51) Int. Cl.
*G01N 33/66* (2006.01)
*G01N 21/64* (2006.01)
(Continued)

(52) U.S. Cl.
CPC .......... *G01N 33/66* (2013.01); *A61B 5/1459* (2013.01); *A61B 5/1473* (2013.01);
(Continued)

(58) Field of Classification Search
None
See application file for complete search history.

(56) References Cited

U.S. PATENT DOCUMENTS

| 4,722,892 A | 2/1988 | Meares et al. |
| 4,861,728 A | 8/1989 | Wagner |
| (Continued) | | |

FOREIGN PATENT DOCUMENTS

| CA | 1329017 | 5/1994 |
| WO | WO 00/043536 | 7/2000 |
| (Continued) | | |

OTHER PUBLICATIONS

"Optical Glucose Sensor Holds Promise For Diabetics And Intensive Care Patients," ScienceDaily, Mar. 17, 2004 <http://web.archive.org/web/20040404161607/http://www.ScienceDaily.com/releases/2004/03/040317073529.htm>, 6 pages.
(Continued)

*Primary Examiner* — Rebecca M Giere
(74) *Attorney, Agent, or Firm* — K&L Gates LLP

(57) ABSTRACT

A method of quantifying the amount of glucose in a sample is provided herein that may further comprise an interferent such as mannitol. At least two measurements are obtained using measurement methods that differ in their sensitivity to the amount of interferent in the sample, thus enabling the results to be compared to determine whether any interferent is present in the sample. A glucose sensor for carrying out a method described herein is also provided.

19 Claims, 8 Drawing Sheets

Related U.S. Application Data

(60) Provisional application No. 61/662,560, filed on Jun. 21, 2012.

(51) Int. Cl.
| | | |
|---|---|---|
| *G01N 21/77* | (2006.01) | |
| *A61B 5/145* | (2006.01) | |
| *A61B 5/1459* | (2006.01) | |
| *A61B 5/1473* | (2006.01) | |
| *G01N 27/327* | (2006.01) | |

(52) U.S. Cl.
CPC ..... *A61B 5/14532* (2013.01); *G01N 21/6428* (2013.01); *G01N 21/7703* (2013.01); *G01N 21/6408* (2013.01); *G01N 27/3271* (2013.01); *G01N 2021/6432* (2013.01); *G01N 2021/6434* (2013.01); *G01N 2021/6441* (2013.01); *G01N 2021/6484* (2013.01); *G01N 2021/772* (2013.01); *G01N 2021/773* (2013.01); *G01N 2021/7786* (2013.01); *G01N 2021/7793* (2013.01)

(56) References Cited

U.S. PATENT DOCUMENTS

| | | | |
|---|---|---|---|
| 4,889,407 | A | 12/1989 | Markle et al. |
| 4,941,308 | A | 7/1990 | Grabenkort et al. |
| 5,012,809 | A | 5/1991 | Shulze |
| 5,047,627 | A | 11/1991 | Yim et al. |
| 5,137,833 | A | 8/1992 | Russell |
| 5,185,263 | A | 2/1993 | Kroneis et al. |
| 5,482,981 | A | 1/1996 | Askari et al. |
| 5,503,770 | A | 4/1996 | James et al. |
| 5,511,408 | A | 4/1996 | Yoshioka et al. |
| 5,512,246 | A | 4/1996 | Russell et al. |
| 5,861,256 | A | 1/1999 | Glass et al. |
| 6,011,984 | A | 1/2000 | Van Antwerp et al. |
| 6,387,672 | B1 | 5/2002 | Arimori et al. |
| 6,627,177 | B2 | 9/2003 | Singaram et al. |
| 6,682,938 | B1 | 1/2004 | Satcher et al. |
| 7,181,096 | B2 | 2/2007 | Matsumoto et al. |
| 7,470,420 | B2 | 12/2008 | Singaram et al. |
| 8,088,097 | B2 | 1/2012 | Markle et al. |
| 8,141,409 | B2 | 3/2012 | Crane et al. |
| 9,151,764 | B2 | 10/2015 | Crane et al. |
| 2002/0119581 | A1 | 8/2002 | Daniloff |
| 2002/0128546 | A1 | 9/2002 | Silver |
| 2005/0158245 | A1 | 7/2005 | Lakowicz et al. |
| 2006/0083688 | A1 | 4/2006 | Singaram et al. |
| 2006/0108218 | A1 | 5/2006 | Gephart et al. |
| 2007/0105176 | A1 | 5/2007 | Ibey et al. |
| 2007/0259441 | A1* | 11/2007 | Saaski ............... G01N 21/553 436/164 |
| 2008/0188725 | A1 | 8/2008 | Markle et al. |
| 2008/0305009 | A1 | 12/2008 | Gamsey et al. |
| 2009/0018418 | A1 | 1/2009 | Markle et al. |
| 2009/0018426 | A1 | 1/2009 | Markle et al. |
| 2009/0177143 | A1 | 7/2009 | Markle et al. |
| 2009/0215646 | A1* | 8/2009 | Anslyn ............ G01N 33/54313 506/12 |
| 2009/0270345 | A1 | 10/2009 | Ketelson et al. |
| 2010/0280184 | A1 | 11/2010 | Crane |
| 2010/0305413 | A1 | 12/2010 | Paterson |
| 2010/0312483 | A1* | 12/2010 | Peyser ................ G01N 33/52 702/19 |
| 2010/0331654 | A1 | 12/2010 | Jerdonek et al. |
| 2011/0044576 | A1 | 2/2011 | Crane |
| 2011/0082356 | A1* | 4/2011 | Yang ................ C12Q 1/006 600/345 |
| 2012/0096918 | A1 | 4/2012 | Crane et al. |
| 2012/0156793 | A1 | 6/2012 | Higgs |

FOREIGN PATENT DOCUMENTS

| | | |
|---|---|---|
| WO | WO 2007/011691 | 1/2007 |
| WO | WO 2008/098087 | 8/2008 |
| WO | WO 2008/141241 | 11/2008 |
| WO | WO 2008/157325 | 12/2008 |
| WO | WO 2009/106805 | 9/2009 |
| WO | WO 2011/097586 | 8/2011 |
| WO | WO 2011/101624 | 8/2011 |
| WO | WO 2011/101626 | 8/2011 |
| WO | WO 2011/113020 | 9/2011 |

OTHER PUBLICATIONS

Baldini and Mignani. "Optical-Fiber Medical Sensors," MRS Bulletin, May 2002, 5 pages.
Bartowsky, Bacterial spoilage of wine and approaches to minimize it, Letters in Applied Microbiology, 48 (2009) 149-156.
International Search Report in International Application No. PCT/GB 2013/051582, dated Apr. 10, 2013, 4 pages.
Ke et al. "A simple and accessible synthetic lectin for glucose recognition and sensing," *Nat. Chem.*, 2012, 4(9):718-723 (Abstract only).
Lee et al., "Colorimetric identification of carbohydrates by a pH indicator/pH change inducer ensemble," *Angewandte Chemie*, Oct. 6, 2006, 45(39):6485-6487.
Liang et al., 6, 6' Bis-substituted BINOL boronic acids as enantioselective and chemoselective fluorescent chemosensors for D-sorbitol, Tetrahedron, 64, 2008, 1309-1315.
Lindner et al., Design and applications of biomimetic anthraquinone dyes: purification of calf intestinal alkaline phosphates with immobilized terminal ring analogues of C.I. reactive Blue 2, *Journal of Chromatography*, 1989, 473(1) :227-240.
Peyser et al., "Use of a Novel Fluorescent Glucose Sensor in Volunteer Subjects with Type 1 Diabetes Mellitus," Journal of Diabetes Science and Technology, vol. 5, Issue 3, May 2011, 687-693.
Schiller et al., "A Fluorescent Sensor Array for Saccharides Based on Boronic Acid Appended Bipyridinium Salts," *Angewandte Chemie*, Aug. 27, 2007, 46(34):6457-6459.
Steiner et al., "Optical Methods for sensing glucose," *Chemical Society Reviews*, Jan. 2011, 40(9):4805-4839.
Wang et al., Boronic Acid-Based Sensors, Current Organic Chemistry, 2002, 6: 1285-1317, Springstein et al., A detailed examination of boronic acid-diol complexation, Tetrahedron 58, 2002, 5291-5300.
Yoon and Czarnik. "Fluorescent chemosensors of carbohydrates. A means of chemically communicating the binding of polyols based on chelation-enhanced quenching," *J. Am. Chem. Soc.* 1992, 114:5874-5875.

\* cited by examiner

GLUCOSE SENSOR

CLAIM OF PRIORITY

This application is a continuation of U.S. application Ser. No. 13/686,760, filed Nov. 27, 2012 (Abandoned), which claims priority under 35 USC § 119(e) to U.S. Patent Application Ser. No. 61/662,560, filed on Jun. 21, 2012, the entire contents of which are hereby incorporated by reference.

FIELD

The document relates to glucose sensors for detecting glucose in a sample that may contain an interferent species, for example mannitol. Methods of quantifying the amount of glucose in such a sample are also provided.

BACKGROUND

Boronic acids are known to form reversible adducts with 1,2- and 1,3-diols. This phenomenon has been utilised by attaching a boronic acid receptor to chromophores or fluorophores in attempts to design sensors for the continuous measurement of glucose. Diboronic acid fluorophore chemistries have also been designed that produce 1:1 adducts with 1,2-diols. Furthermore, if the diboronic acid is linked to the fluorophores via a short linker, then the chemistry operates by a Photo-induced Electron Transfer ("PET") mechanism.

There has been an enormous drive to utilise these chemistries in the development of sensors to measure physiological glucose. The focus has been to improve the accuracy and reliability for calculating a glucose concentration.

SUMMARY

Interferent species can sometimes be present in significant quantities in the blood. For example, mannitol can be present in a clinical setting. Interferent species, including mannitol, can be capable of competing with glucose for binding to the boronic acid receptor in a glucose sensor.

Interferent species, such as mannitol, can lead to errors during glucose sensing methods. Some potential interferents, such as saccharides (e.g., mannitol), have a similar molecular weight and chemical structure to glucose. Thus, although protective barrier layers can be used to block some potential interferents, certain potential interferents, including mannitol, can permeate glucose permeable barrier layers. Where significant errors arise during monitoring of a patient's glucose levels (e.g., due to the presence of an interferent such as mannitol in the blood), potentially dangerous mis-diagnoses and/or patterns of medical treatment can arise.

Glucose sensors and methods provided herein therefore address the problem of inaccuracies arising during glucose sensor indicating chemistry, in particular where these inaccuracies arise due to the presence of an interferent in the sample.

Methods provided herein can include obtaining two measurements of the amount of glucose using both a first and a second measurement method, which methods differ in their sensitivity to the amount of interferent in the sample. Comparison between the two measurements can be used to determine whether any interferent is present in the sample and, if so, for suitable steps to be taken to address this issue, e.g., for an accurate assessment of the glucose concentration in the sample to be obtained.

Thus, a method of quantifying the amount of glucose in a sample that may further include an interferent can include:
inserting into the sample a glucose sensor comprising:
a sensing region comprising at least a first indicator system including a first receptor for binding to glucose and a first fluorophore associated with the first receptor; and
an optical waveguide for directing light onto the sensing region; providing incident light to the sensing region of the sensor and obtaining a first measurement of the amount of glucose by a first measurement method including detecting the emission of said first fluorophore;
obtaining a second measurement of the amount of glucose by a second measurement method, wherein the second measurement method differs in its sensitivity to the amount of said interferent in the sample from the first measurement method; and
comparing said first measurement and said second measurement and thereby determining whether any said interferent is present in the sample;
wherein said interferent is a substance that is capable of interfering with the binding of glucose to said first receptor.

In some cases, methods provided herein include:
inserting into the sample a glucose sensor comprising:
a sensing region including:
a first indicator system including a first receptor for binding to glucose and a first fluorophore associated with the first receptor, wherein said first receptor has an association constant KG1 with glucose and an association constant $K_{M1}$ with said interferent, and
a second indicator system including a second receptor for binding to glucose and a second fluorophore associated with the second receptor, wherein said second receptor has an association constant $K_{G2}$ with glucose and an association constant $K_{M2}$ with said interferent, and wherein $K_{G2}/K_{M2}$ is different from $K_{G1}/K_{M1}$; and
an optical waveguide for directing light onto the sensing region;
providing incident light to the sensing region of the sensor;
obtaining a first measurement of the amount of glucose by a first measurement method including detecting the emission of said first fluorophore;
obtaining a second measurement of the amount of glucose by a second measurement method including detecting the emission of said second fluorophore; and
comparing said first measurement and said second measurement, thereby determining whether any of said interferent is present in the sample, and
correcting for the presence of any said interferent in the sample.

This preferred method is particularly advantageous because a single experimental protocol can be used simultaneously to obtain the first and the second measurements, namely an emission fluorescence technique which involves providing incident light to the sensing region of the sensor (in a single step) and detecting (in a single emission spectrum/single emission measurement) the emission of both the first and the second fluorophore. Comparison between the fluorescence of the two fluorophores can permit for correction (elimination) of any interferent contribution to the fluorescence of the system, as further described herein.

Thus, in this preferred method there is no need for a separate experimental verification of the interferent content of the sample, for example by taking a blood sample and subjecting it to laboratory analysis (e.g., by electrochemical methods). Consequently, the preferred method of the document is particularly convenient, rapid and easy to operate (e.g., without the presence of specially trained medical practitioners).

The present document also provides a related a glucose sensor, specifically a glucose sensor for quantifying the amount of glucose in a sample that may further include an interferent, the sensor including:
a sensing region including:
a first indicator system including a first receptor for binding to glucose and a first fluorophore associated with the first receptor, wherein said first receptor has an association constant $K_{G1}$ with glucose and an association constant $K_{M1}$ with said interferent, and
a second indicator system including a second receptor for binding to glucose and a second fluorophore associated with the second receptor, wherein said second receptor has an association constant $K_{G2}$ with glucose and an association constant $K_{M2}$ with said interferent, and
wherein $K_{G2}/K_{M2}$ is different from $K_{G1}/K_{M1}$; and
an optical waveguide for directing light onto the sensing region.

This glucose sensor can be used to carry out the preferred method of the document.

Further preferred features and embodiments are described in the accompanying description and the appended claims.

DETAILED DESCRIPTION

A method described herein can include the use of a glucose sensor including a sensing region including at least a first indicator system including a first receptor for binding to glucose and a first fluorophore associated with the first receptor; and an optical waveguide for directing light onto the sensing region.

A method described herein can use fibre optic glucose sensors (i.e., a glucose sensor where the optical waveguide is an optical fibre), but the presently described methods can also be carried out with sensors having different types of optical waveguides.

Glucose sensing methods described herein can be carried out in an aqueous solution. In some cases, glucoses sensing methods described herein can be carried out in bodily fluids such as interstitial tissue or blood. For example, the glucose sensors described herein can be used as invasive sensors and inserted into a blood vessel. Glucose sensing methods provided herein can use non-invasive sensors for in vitro use, implantable sensors, and/or subcutaneous sensors.

Figure 1:
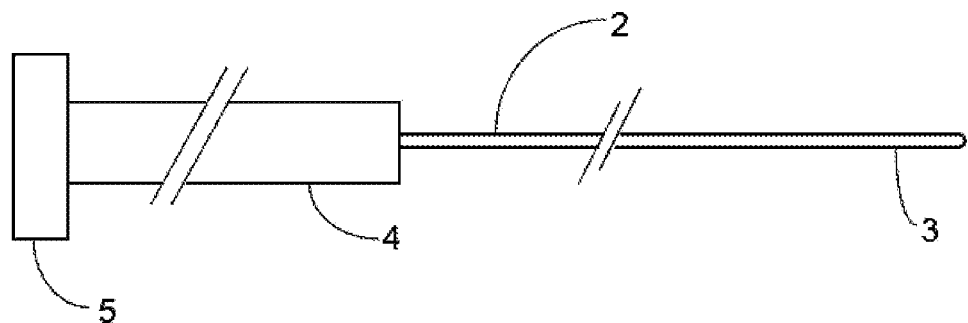
FIGS. 1 and 1a depict a sensor incorporating an optical fibre and a monitor for such a sensor.
Figure 1A:
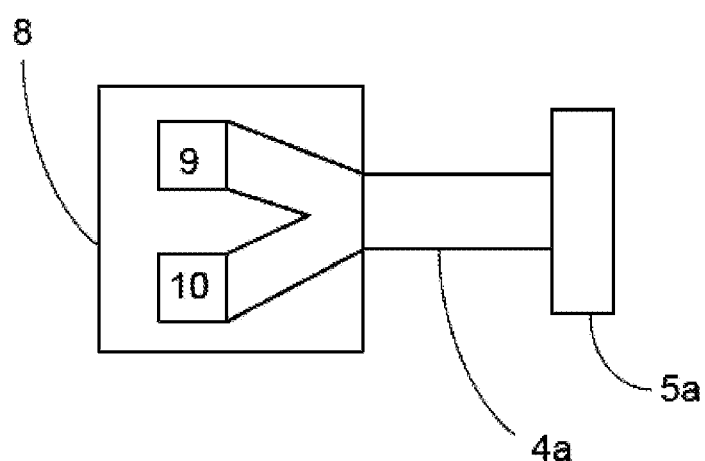

An example a sensor incorporating an optical fibre is depicted in FIGS. 1 and 1a. The sensor 1 includes an optical fibre 2 including a sensing region 3 at its distal end. In some cases, sensor 1 can be an invasive sensor. Sensor 1 includes a fibre 2. Fibre 2 can be adapted for insertion into a patient, for example insertion into a blood vessel through a cannula. The sensing region 3 (depicted in more detail in FIGS. 2, 3 and 3a) contains a cell or chamber 7 in which the, or each, indicator system is contained. The optical fibre extends through cable 4 to connector 5 which is adapted to mate with an appropriate monitor 8. The monitor can include a further optical cable 4a that mates with the connector at 5a and at the other bifurcates to connect to (a) an appropriate source of incident light for the optical sensor 9 and (b) a detector for the return signal 10.

In some embodiments, the sensor is a disposable sensor. A disposable sensor can be adapted to be connected to a non-disposable monitor including a light source 9 and detector 10.

Figure 2:
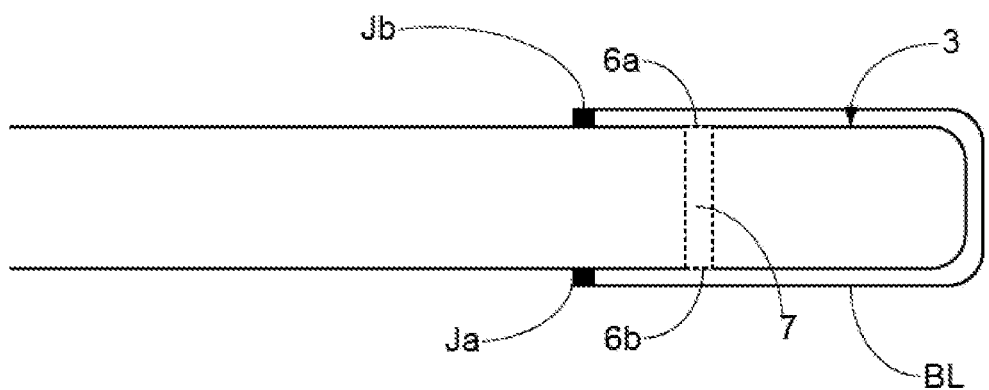
FIGS. 2, 3 and 3a depict various embodiments of a sensing region of a sensor.

As depicted in FIG. 2, the sensing region 3 incorporates a cell 7 in the form of a chamber within the fibre. The cell may take any form, as long as the one or more indicator systems are contained in the path of the incident light directed by the waveguide (e.g., a fibre). Thus, the cell may be attached to the distal end of the fibre or waveguide or may be in the form of a chamber within the fibre having any desired shape.

Optionally, a reactive oxygen species ("ROS") quenching agent may be present in the sensor, for example within the sensing region or within an optional barrier layer as further described herein. An example of a reactive oxygen species is hydrogen peroxide ($H_2O_2$). Suitable ROS-quenching agents are as described in U.S. patent application No. 61/524,525 and PCT/GB2012/051921, the contents of which are incorporated by reference herein. Suitable means for incorporating the ROS-quenching agent into a glucose sensor are also described in U.S. patent application No. 61/524,525 and PCT/GB2012/051921 and again are incorporated by reference herein.

The sensing region 3 of the glucose sensor has one or more openings 6a, 6b to enable glucose to enter the cell. A glucose permeable barrier layer "BL" may optionally be provided across these openings so that glucose enters the cell through the barrier layer. A glucose permeable barrier layer used in a glucose sensor provided herein can be capable of at least partially restricting the passage of high molecular weight materials such as proteins.

Figure 3:
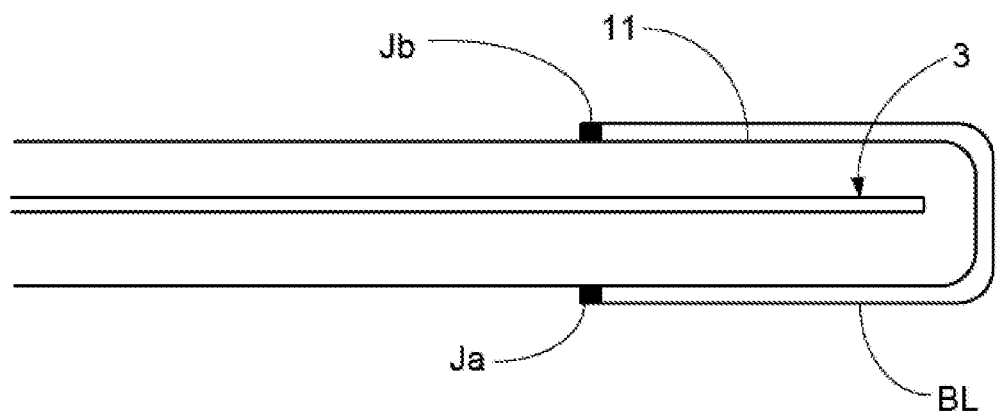
Figure 3A:
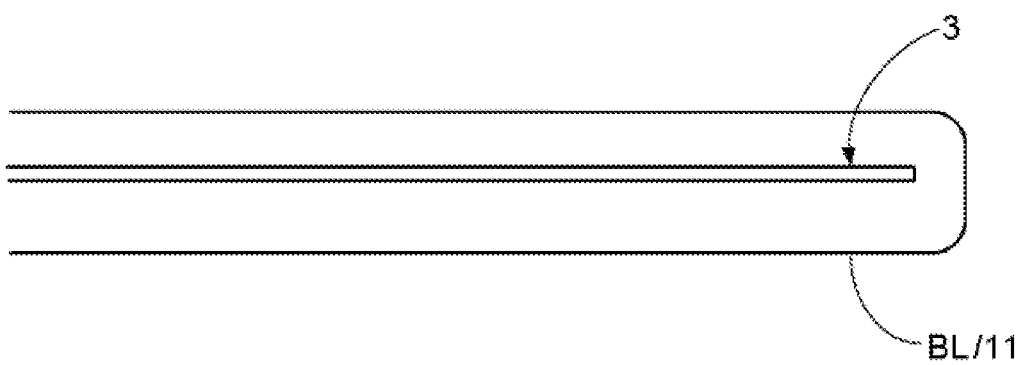

In FIGS. 2, 3 and 3a, the optional barrier layer BL is provided over the entire sensing region 3. Alternatively, however, the optional barrier layer BL may be provided on only part of the sensing region, for example only across openings 6a and 6b.

Briefly, FIG. 2 shows an embodiment in which the optional barrier layer BL is applied directly onto the sensing region 3, here onto the tip of the optical fibre, via joints (e.g., thermoformed attachment points) Ja and Jb. In FIG. 3, the sensing region 3 is provided within a separate support 11 and the barrier layer BL is provided on the support 11 (again via joints Ja and Jb). In FIG. 3a, the barrier layer itself forms a support structure "BL/11". Further details on suitable sensor constructions when a barrier layer is incorporated, and on suitable materials for such barrier layers, are described in U.S. patent application No. 61/524,525, PCT/GB2012/051921 and WO2011/101626, the contents of which are incorporated by reference herein.

Glucose sensors having design features in addition to or different from those shown in the attached Figures are of course possible, provided that these include both of the required: (i) sensing region including at least a first indicator system including a first receptor for binding to glucose and a first fluorophore associated with the first receptor; and (ii) optical waveguide for directing light onto the sensing region. For example, glucose sensors such as those described and illustrated in WO2008/141241, WO2008/098087 and WO2011/113020 can be used.

By "indicator system" is meant a combination of a receptor for binding to glucose and a fluorophore associated therewith, such that the emission pattern (e.g. the wavelength, intensity, lifetime) of the fluorophore is altered when glucose is bound to the receptor (thus enabling the emission behaviour of the fluorophore to act as an "indicator" for the presence of glucose).

The first receptor and first fluorophore may be directly bonded to one another as a first receptor-first fluorophore construct. Examples of suitable first fluorophores include anthracene, pyrene and derivatives thereof. Examples of suitable first receptors are boronic acid receptors, such as compounds having at least one (for example one or two), or at least two (for example two or three) boronic acid groups.

Suitable receptors also include arsenic-containing receptors, tellurium-containing receptors and germanium-containing receptors, for example receptors comprising one or more groups of formula $H_3AsO_3$, $H_2AsO_3-$, $H_6TeO_6$, $H_5TeO_6-$, $Ge(OH)_6$ or $GeO(OH)_3-$, or derivatives thereof. Examples of such receptors include the receptors disclosed in US 2005/0158245, the content of which is herein incorporated by reference in its entirety. Still further suitable receptors include synthetic lectins that are capable of binding to glucose, for example via non-covalent interactions such as hydrogen bonding, CH-π interactions and/or hydrophobic interactions. Examples of such synthetic lectins are described in Nat Chem. 2012 4(9) 718-23, the content of which is herein incorporated by reference in its entirety.

In a preferred embodiment, the first receptor is a group of formula (I)

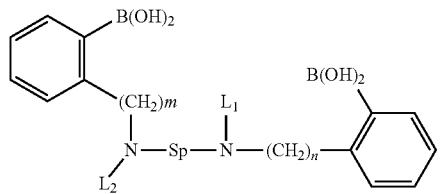

(I)

wherein m and n are the same or different and are typically one or two, preferably one; Sp is an aliphatic spacer, typically an alkylene moiety, for example a $C_1$-$C_{12}$ alkylene moiety, e.g. a $C_6$ alkylene moiety; and $L_1$ and $L_2$ represent possible points of attachment to other moieties, for example to a fluorophore or to a hydrogel. For example, $L_1$ and $L_2$ may represent an alkylene, alkylene-arylene or alkylene-arylene-alkylene moiety, linked to a functional group. Where no attachment to another moiety is envisaged, the functional group is protected or replaced by a hydrogen atom. Typical alkylene groups for $L_1$ and $L_2$ are $C_1$-$C_4$ alkylene groups, e.g. methylene and ethylene. Typical arylene groups are phenylene groups. The functional group is typically any group which can react to form a bond with, for example, the fluorophore or hydrogel, e.g. ester, amide, aldehyde or azide. Varying the length of the spacer Sp alters the selectivity of the receptor. A $C_6$-alkylene chain can provide a receptor which has good selectivity for glucose. Further details of such receptors are found in U.S. Pat. No. 6,387,672, the contents of which are incorporated herein by reference in their entirety.

Further examples of first receptors suitable for the presently described sensors include those of formula (II):

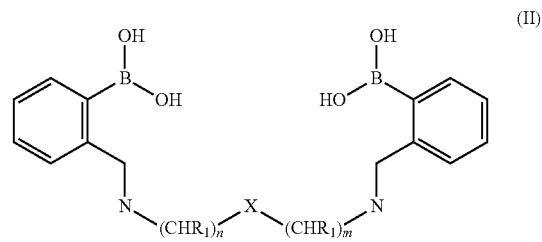

(II)

wherein X represents O, S, $NR_2$ or $CHR_3$;
n is from 1 to 4;
m is from 1 to 4, and n+m is 5;
$R_2$ represents hydrogen or $C_{1-4}$ alkyl;
each $R_1$ is the same or different and represents hydrogen, $C_{1-4}$ alkyl or $C_{3-7}$ cycloalkyl;
or $R_1$, together with an adjacent $R_1$, $R_2$ or $R_3$ group and the carbon or nitrogen atoms to which they are attached, form a $C_{3-7}$ cycloalkyl or a 5- or 6-membered heterocyclyl group,
wherein when X represents $CHR_3$, $R_3$ together with an adjacent $R_1$ group and the carbon atoms to which they are attached form a $C_{3-7}$ cycloalkyl group. Further details of receptors of this type are found in U.S. 61/431,756, the contents of which are incorporated herein by reference.

An example of a boronic acid receptor having one boronic acid group is a compound of the formula (III) below

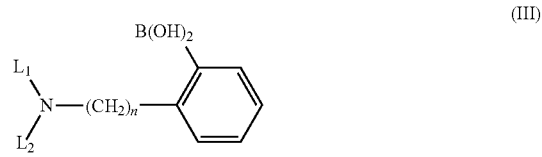

(III)

wherein:
n is from one to three, preferably one or two, and more preferably one; and
$L_1$ and $L_2$ represent possible points of attachment to other moieties, for example to a fluorophore or to a hydrogel. For example, $L_1$ and $L_2$ may represent an alkylene, alkylene-arylene or alkylene-arylene-alkylene moiety, linked to a functional group. Where no attachment to another moiety is envisaged, the functional group is protected or replaced by a hydrogen atom. Typical alkylene groups for $L_1$ and $L_2$ are $C_1$-$C_4$ alkylene groups, e.g. methylene and ethylene. Typical arylene groups are phenylene groups. The functional group is typically any group which can react to form a bond with, for example, the fluorophore or hydrogel, e.g. ester, amide, aldehyde or azide.

As explained above, the first receptor may be a compound having one boronic acid group such as that of formula (III). However, more typically the first receptor includes two boronic acid groups. As explained in further detail below, where a second receptor is additionally present, this second receptor may be a compound having one boronic acid group, such as a compound of formula (III).

As used herein the term alkyl or alkylene is a linear or branched alkyl group or moiety. An alkylene moiety may, for example, contain from 1 to 15 carbon atoms such as a $C_{1-12}$ alkylene moiety, $C_{1-6}$ alkylene moiety or a $C_{1-4}$ alkylene moiety, e.g. methylene, ethylene, n-propylene, i-propylene, n-butylene, i-butylene and t-butylene. $C_{1-4}$ alkyl is typically methyl, ethyl, n-propyl, i-propyl, n-butyl or t-butyl. For the avoidance of doubt, where two alkyl groups or alkylene moieties are present, the alkyl groups or alkylene moieties may be the same or different.

An alkyl group or alkylene moiety may be unsubstituted or substituted, for example it may carry one, two or three substituents selected from halogen, hydroxyl, amine, ($C_{1-4}$ alkyl) amine, di($C_{1-4}$ alkyl) amine and $C_{1-4}$ alkoxy. Preferably an alkyl group or alkylene moiety is unsubstituted.

As used herein an arylene group is an unsaturated group which may be monocyclic, bicyclic, or which may contain three or four fused rings. Typically, an arylene group is phenylene. Arylene groups may be unsubstituted or substituted. Suitable substituents are $C_{1-4}$ alkyl groups, for example methyl and ethyl. Preferably, an arylene group is unsubstituted.

As used herein a $C_{3-7}$ cycloalkyl group is typically a cyclopentyl or cyclohexyl group. $C_{3-7}$ cycloalkyl groups may be unsubstituted or substituted. Suitable substituents are $C_{1-4}$ alkyl groups, for example methyl and ethyl. Preferably, a $C_{3-7}$ cycloalkyl group is unsubstituted. As used herein a 5- or 6-membered heterocyclyl group is a 5- or 6-membered saturated ring containing one or more, typically one or two, e.g. one, heteroatom selected from N, O and S. Preferred heterocyclyl groups are those containing a nitrogen atom, for example piperidinyl and pyrrolidinyl. Heterocyclyl groups may be unsubstituted or substituted. Suitable substituents are $C_{1-4}$ alkyl groups, for example methyl and ethyl. Preferably, a heterocyclyl group is unsubstituted.

The first receptor and first fluorophore are typically bound to one another and may further be bound to a polymeric matrix such as a hydrogel, or to a dendrimer. Examples of suitable hydrogels and dendrimers are those described in WO 2011/101624, the content of which is incorporated herein by reference.

Alternatively, the first receptor and first fluorophore may be not directly bonded to one another (for example, they may be not bonded to one another or they may be bonded only via a polymeric chain such as a polymeric chain contained within a hydrogel matrix). It will be clear that when the first receptor and first fluorophore are not directly bonded to one another, they must still be capable of interacting in such a way that the fluorescence behaviour of the first fluorophore changes when the indicator system is exposed to glucose. For example, the first fluorophore and the second fluorophore may be capable of binding electrostatically (e.g., as a charge pair), which binding is capable of being at least partly disrupted by the presence of glucose. Examples of suitable first fluorophores include pyranine (HPTS) and its derivatives, such as HPTS itself and the derivatives HPTS-PEG, HPTS-MA, HPTS-$CO_2$, HPTS-Tri-Cys-MA and HPTS-LysMA disclosed in US 2009/0177143, the content of which is herein incorporated by reference in its entirety. Further suitable first fluorophores may include the SNAF and SNAFL dyes commercially available from Molecular Probes. Examples of suitable first receptors include aromatic boronic acids covalently bonded to a conjugated nitrogen-containing heterocyclic aromatic bisonium structure (e.g. a viologen). Examples of such first receptors are provided in US 2009/0177143, the content of which is herein incorporated by reference in its entirety. One particularly suitable first receptor is 3,3'-oBBV, as described in US 2009/0177143.

As used herein, the phrase "in vivo sample" means that the sample is a sample that is present in the human or animal (preferably human) body. For example, such a sample may be a bodily fluid such as the blood that is present in the human or animal (preferably human) body. An in vivo sample can be contrasted with an ex vivo sample, for example an ex vivo blood sample, wherein the sample has been removed (isolated) from the human or animal body. Consequently, references throughout this specification to methods carried out on an "in vivo sample" mean that the method is a method of quantifying the amount of glucose in the human or animal (preferably human) body. It should be clarified, however, that an in vivo sample can be subject to glucose (or interferent, e.g. mannitol interferent) measurement either by directly measuring the glucose concentration in vivo, for example using an invasive method as described herein, or by extracting the sample from the body and measuring the glucose concentration in vitro. In the latter case, the glucose (or interferent, e.g. mannitol interferent) concentration of the sample as measured corresponds to the concentration of the in vivo sample at the time point at which it was extracted from the body.

It follows from the above that an in vivo sample as used herein will vary in terms of its glucose and interferent (e.g., mannitol) concentration over time due to, for example, metabolism of the interferent (e.g., mannitol) in the body. Accordingly, where the presently described methods take two or more measurements of an in vivo sample at different points in time, the sample will not necessarily have the same composition at those different time points.

To the extent that the methods of the document are carried out on in vivo samples, all of the procedures carried out in accordance with the methods provided herein (including inserting into the sample a glucose sensor and electrochemically measuring the amount of glucose or interferent in the sample) are routine procedures that do not involve any substantial health risk to the human or animal patient and which moreover can be carried out without substantial medical expertise. It will be appreciated that steps such as insertion of a cannula (for example, in the context of inserting an exemplary glucose sensor of the present document) and extraction of blood samples for the purposes of obtaining electrochemical measurements (e.g., by needle extraction) are routine in the art and can be carried out for example by a nurse rather than requiring the involvement of doctors. Thus, the methods provided herein do not constitute surgical methods carried out on the human or animal body.

The methods provided herein can provide incident light to a sensing region of a sensor and a first measurement of the amount of glucose is obtained by a first measurement method including detecting the emission of said first fluorophore.

The first measurement method may comprise making an equilibrium measurement of the emission of the first fluorophore after the glucose sensor has been contacted with the sample.

In one aspect, the first indicator system may comprise a first receptor that is capable of at least partially quenching the fluorescence emission of the first fluorophore when the said first fluorophore is exposed to excitation light (e.g., by association of the receptor with a quencher). In this aspect, when the glucose sensor is contacted with the sample, glucose in the sample binds with the first receptor and thereby at least partially reduces the quenching efficiency of the first receptor, thus leading to an enhancement in emission from the first fluorophore.

The first measurement method may use a dye displacement technique.

In the light of the discussion herein, it will be appreciated that this first measurement may contain a contribution arising from binding of an interferent (one example of which is mannitol), rather than the desired glucose, to the receptor when there is an interferent present in the sample. In other words, the first measurement may not of itself be capable of providing an accurate quantitative determination of the glucose concentration in a sample that contains interferent (i.e., without taking further steps to account for the presence of interferent).

Figure 4:
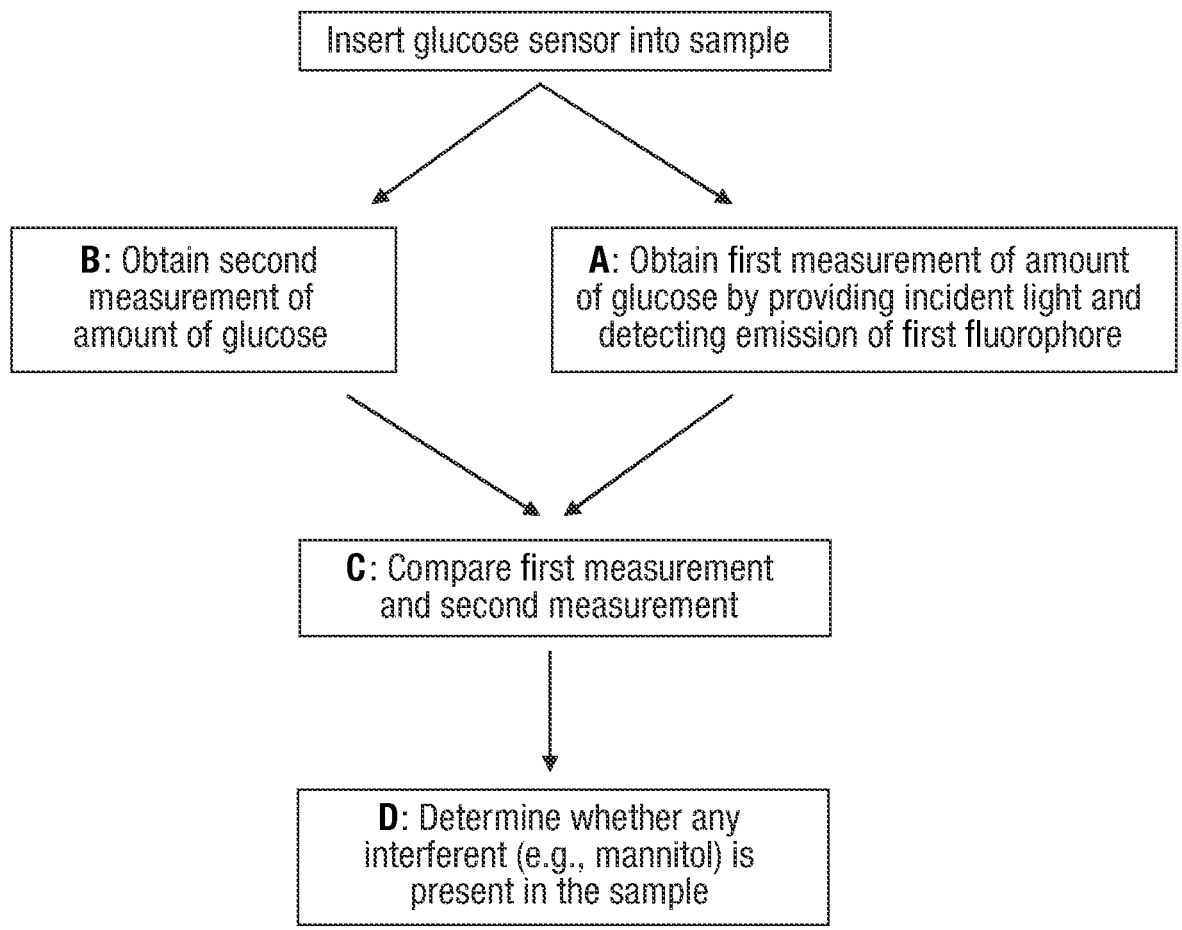
FIG. 4 depicts a flow chart that schematically illustrates a method provided herein.

Accordingly, the methods provided herein further include obtaining a second measurement of the amount of glucose by a second measurement method, as shown schematically in the flow chart of FIG. 4. The nature of the second measurement method is not critical. The methods provided herein are capable of quantitatively determining the quantity of glucose in a sample.

The second measurement method differs in its sensitivity to the amount of interferent in the sample from the first measurement method. By "differs in its sensitivity to the amount of interferent" it is meant that for a sample that does contain some interferent, the contribution made by that interferent to the second measurement, relative to the contribution made by the glucose, is different from the corresponding contribution in the first measurement.

It can easily be established by one of ordinary skill in the art whether two measurement methods "differ in sensitivity to the amount of interferent in the sample". For example, when the second measurement method is an electrochemical method, then typically that second measurement method will be sensitive only to the analyte (i.e., usually glucose, though possibly the interferent) that it is probing, thereby rendering it necessarily different in sensitivity to the amount of interferent in the sample from the first measurement method. When the second measurement method includes detecting the emission of a second fluorophore in a second indicator system, typically both the first and second indicator systems are pre-calibrated to assess their detection sensitivities to glucose and the interferent, and the first indicator system's detection sensitivities to glucose and interferent are different from the second indicator detection sensitivities to glucose and interferent.

Usually both the first and second measurement methods are capable of "direct" measurement of the amount of glucose in a sample, i.e. both the first and second measurement methods are sensitive to the amount of glucose in the sample and therefore can, in the absence of interferent, be used to determine quantitatively the concentration of glucose in a sample.

However, it will be appreciated that the methods provided herein can also be carried out when the second measurement method is sensitive to the interferent concentration, but is actually substantially or completely insensitive to glucose concentration. For example, the second measurement method in certain cases directly indicates only the concentration of the interferent, but clearly still allows for comparison with the first measurement so as to determine whether any said interferent is present. In other words, the second measurement method can provide an "indirect", rather than a "direct" second measurement of the amount of glucose. For the avoidance of doubt, it is emphasised that the methods provided herein can use a second measurement of an amount of glucose that is direct (the second measurement including a glucose contribution) or a second measurement of an amount of glucose that is indirect (the second measurement including no glucose contribution).

Figure 5:
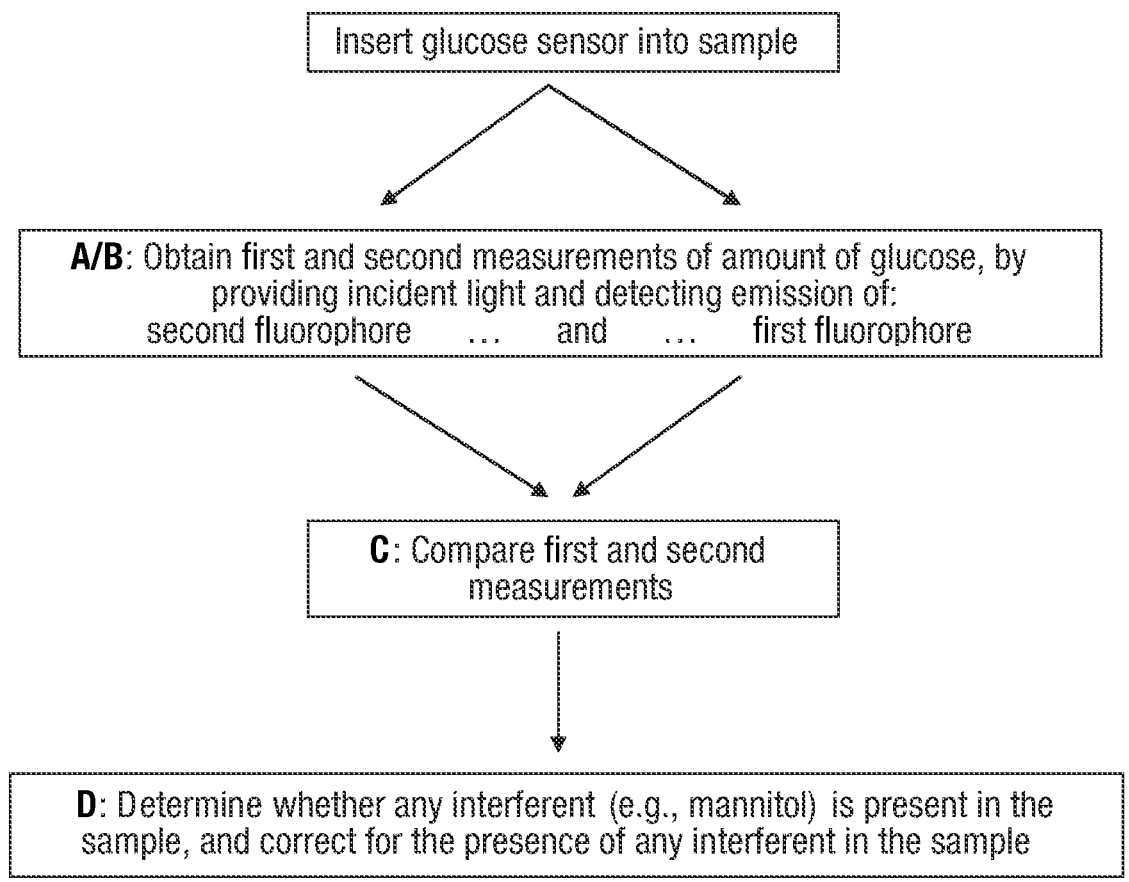
FIG. 5 depicts a flow chart that schematically illustrates one embodiment of the a method provided herein.
Figure 6:
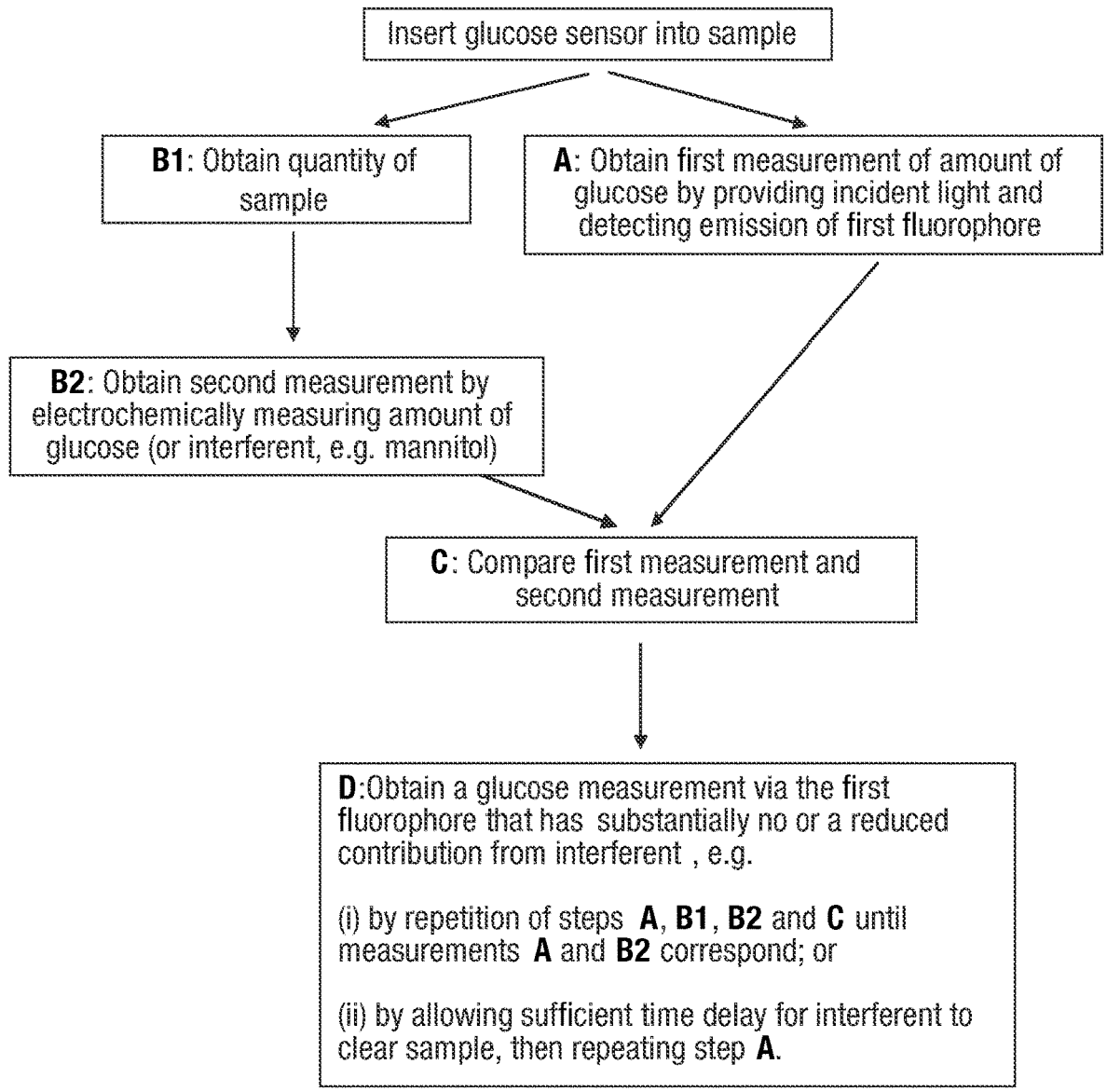
FIG. 6 depicts a flow chart that schematically illustrates another embodiment of a method provided herein.
Figure 7A:
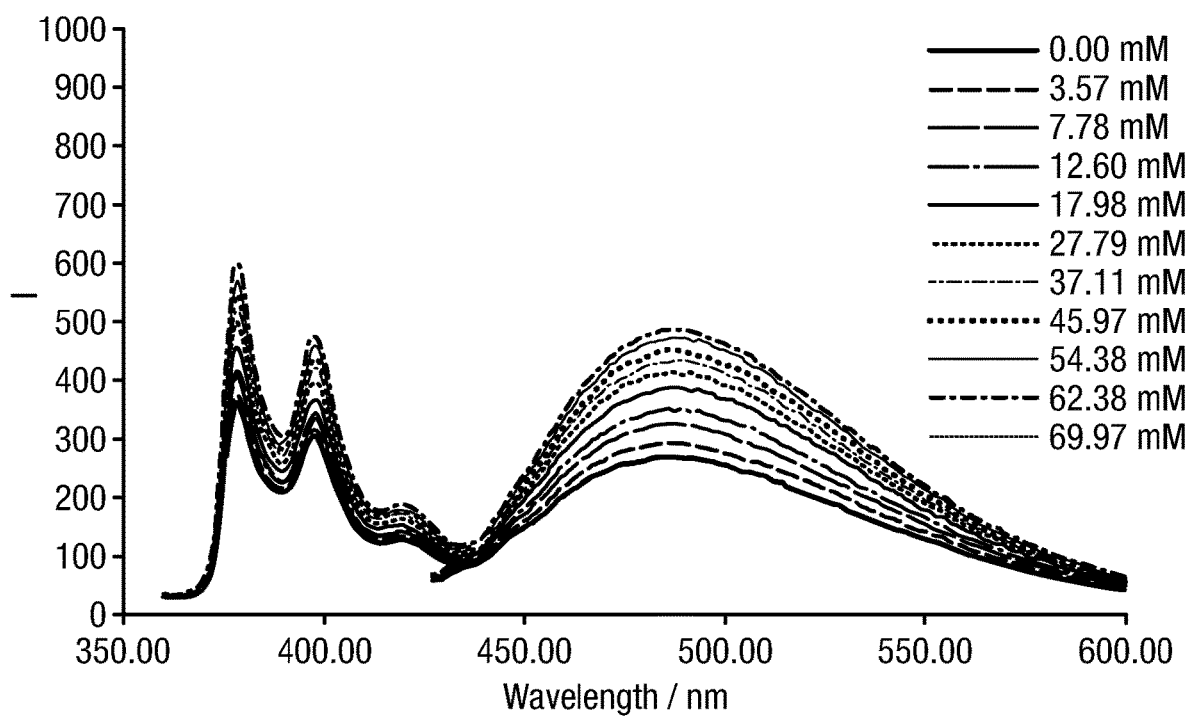
FIGS. 7a-7d depict the results of Example 2 as follows: A) Fluorescence emission spectra recorded in the binding study of hydrogel 4 vs. D-glucose in PBS at excitation wavelengths of 350 and 405 nm and at [D-glucose]$_{titrant}$ of 214 mM (note that lower lines to upper lines follow in order of lower concentrations to high concentrations); B) Fluorescence emission spectra recorded in the binding study of hydrogel 4 vs. D-mannitol in PBS at excitation wavelengths of 350 and 405 nm and at [mannitol]$_{titrant}$ of 184 mM (note that lower lines to upper lines follow in order of lower concentrations to high concentrations); C) Relative fluorescence intensity versus carbohydrate concentration profile of hydrogel 4 vs. D-glucose, $\lambda_{ex}$=350 nm, $\lambda_{em}$=380 nm and $\lambda_{ex}$=405 nm, $\lambda_{em}$=487 nm; and D) Relative fluorescence intensity versus carbohydrate concentration profile of hydrogel 4 vs. D-mannitol, $\lambda_{ex}$=350 nm, $\lambda_{em}$=380 nm and $\lambda_{ex}$=405 nm, $\lambda_{em}$=487 nm.
Figure 7B:
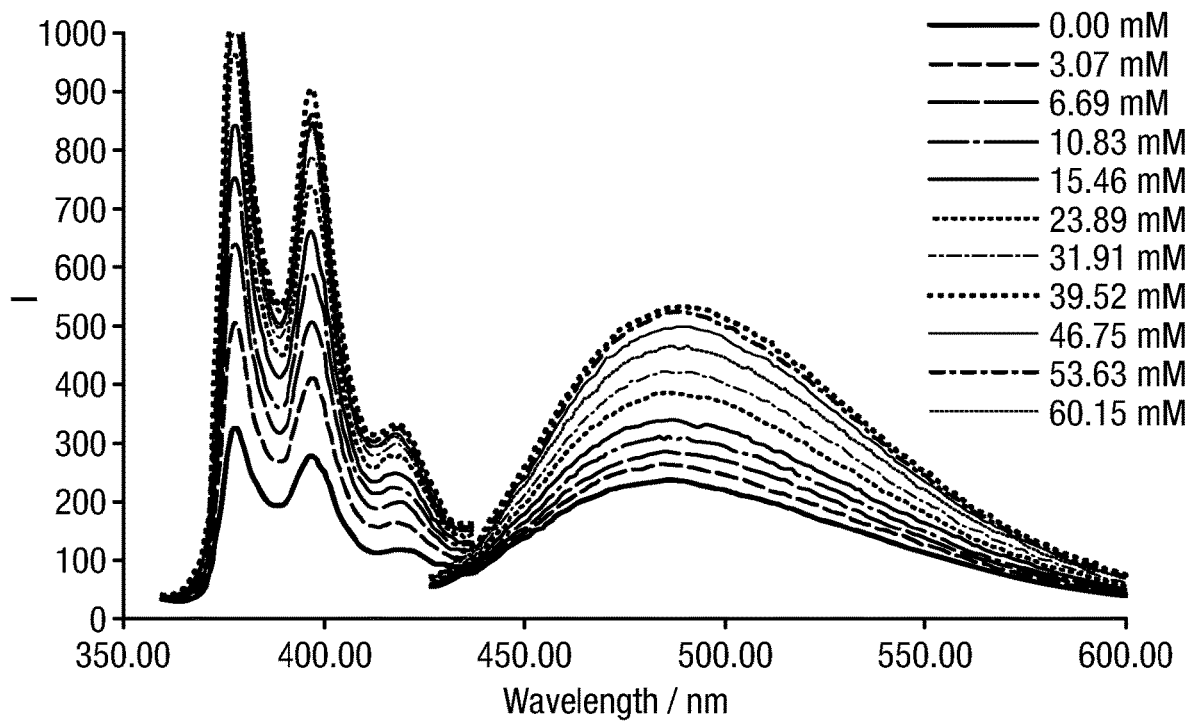
Figure 7C:
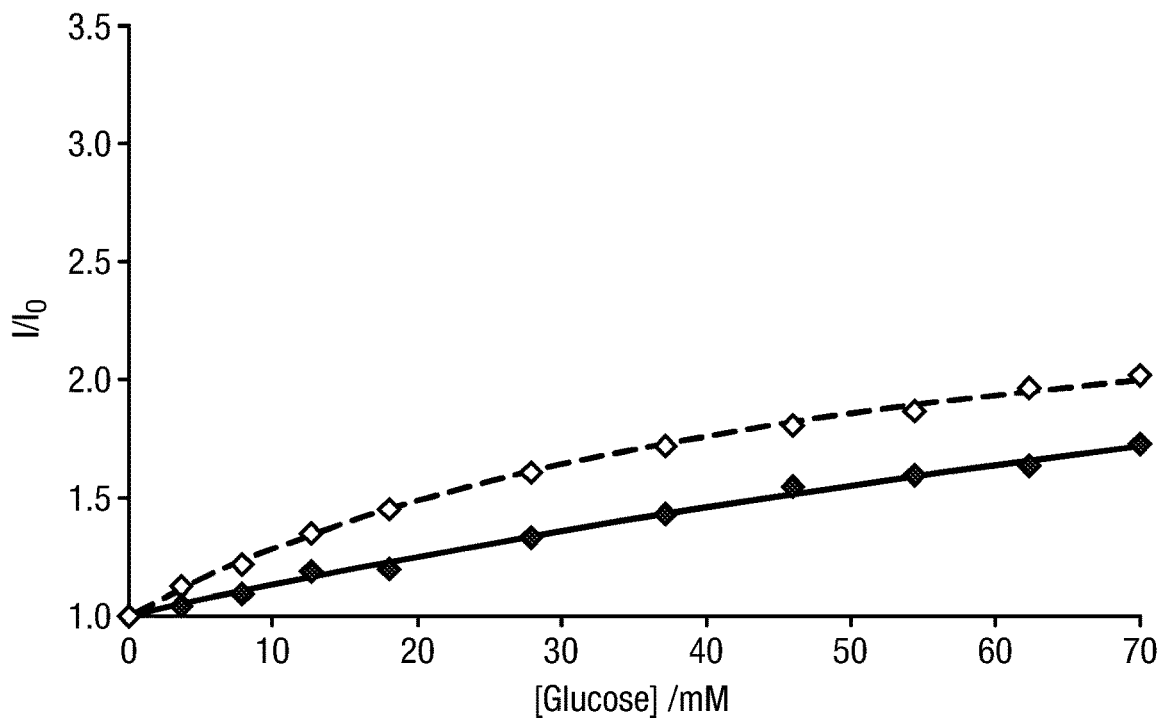
Figure 7D:
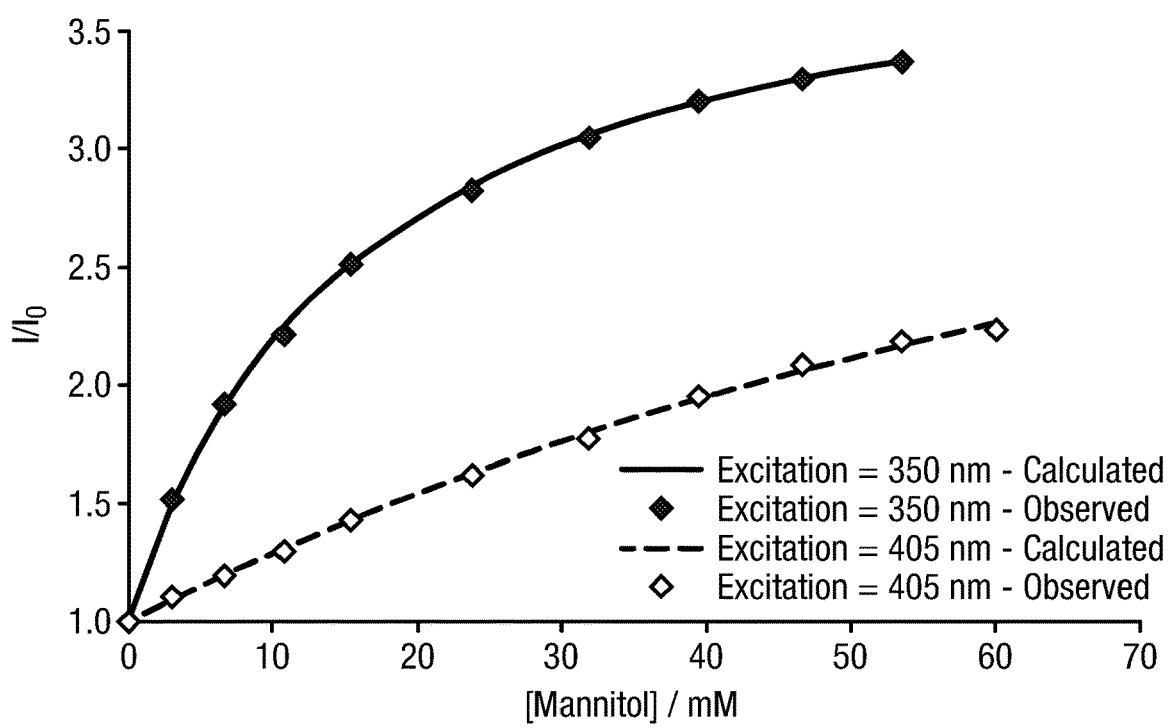

The second measurement method used in the methods provided herein may for example include electrochemically measuring the amount of glucose (or interferent) in the sample (as shown schematically in the flow chart of FIG. 6). In some cases, the second measurement method may for example include detecting the emission of a second fluorophore included in a second indicator system including a second receptor for binding to glucose and a second fluorophore (as shown schematically in the flow chart of FIG. 5). These exemplary second measurement methods will now be discussed in turn.

Electrochemical Second Measurement Methods

Electrochemically measuring the amount of glucose in the sample can be achieved using well known techniques in the art for electrochemical detection of glucose. Commercially available glucose sensors working on electrochemical principles can be used to carry out the methods provided herein. Exemplary devices for electrochemical glucose detection are the analyzers provided by YSI™ Life Sciences. In some cases, these devices have a small amount of (ex vivo) sample inputted, from which glucose concentration can then accurately be determined. For example, when carrying out a real-time in vivo analysis of glucose concentration using the glucose sensor described herein, a blood sample may be extracted from the patient and used for the electrochemical analysis.

In some cases, methods provided herein use a second measurement method that electrochemically measures an amount of the interferent in the sample. It will be appreciated this corresponds to the "indirect" second measurement of glucose described herein.

In some cases, an amount of glucose in an in vivo sample is determined using the methods described herein using a second measurement method that includes electrochemically measuring the amount of glucose (or interferent) in the sample. Methods described herein can rely on in vivo metabolic clearance of any of the interferent initially present in the sample over time, such methods of course therefore being suitable specifically for interferents that are capable of being metabolically cleared (i.e., metabolised). Methods described herein can obtain the final, quantified glucose concentration once the interferent has been at least substantially metabolised.

In some cases, a second measurement method used in a method provided herein includes electrochemically measuring the amount of glucose (or interferent) in the sample, the method including:

(i) obtaining said first measurement at a time point $t_{test}$;
(ii) obtaining said second measurement by said second measurement method, wherein said second measurement method includes electrochemically measuring the amount of glucose, or interferent, in the sample at said time point $t_{test}$; and (iii) comparing said first measurement and said second measurement, thereby determining whether said first measurement contains a contribution from the interferent in the sample.

Methods provided herein can be carried out on a human or animal subject and the sample is an in vivo bodily fluid of said subject. For example, step (i) can include carrying out an in vivo measurement on said bodily fluid at time $t_{test}$ (e.g. an invasive measurement as described herein, or any other method carried out directly on the body without extracting the sample). Step (ii) can include extracting a portion of said bodily fluid from said subject at time $t_{test}$ and carrying out an in vitro electrochemical measurement thereon.

In some cases, results obtained at $t_{test}$ can be used to establish whether the interferent is having a significant adverse effect on (i.e., making a significant interfering contribution to) the glucose concentration as measured by the (fluorescence emission) glucose sensor.

The reference to "electrochemically measuring the amount of glucose, or interferent, in the sample at said time point $t_{test}$" means obtaining an electrochemical measurement of the amount of glucose, or interferent, that was present in the sample at the time point $t_{test}$. The electrochemical measurement can be obtained by obtaining a quantity of the sample, e.g. by needle extraction in the case of an in vivo sample, and then by electrochemically measuring the amount of glucose, or interferent, therein.

If the comparison step (iii) indicates that there is no significant interferent contribution to the first measurement, then there is no need for further steps to occur (it having been confirmed that the first measurement is accurate). It will of course be appreciated that during practical use of the glucose sensor, this means that ongoing (continuous) measurement of glucose concentration over a prolonged period can be carried out using the first indicator system, it now having been established that there is no danger of a false reading due to unmetabolised interferent in the sample.

If the comparison step (iii) indicates that there is a significant interferent contribution to the first measurement, a skilled person (e.g., a nurse) can identify that the accuracy of the glucose concentration measurement from the glucose sensor is compromised by the interferent. The skilled person may determine that an accurate measurement using the glucose sensor should be taken at a later time when the interferent has (at least partially) been metabolised and therefore been eliminated from the in vivo system. In some cases, an estimated time for interferent elimination from the in vivo system can be calculated by the skilled person (e.g., a nurse) and/or by a sensor provided herein. For example, the sensor provided herein can be connected to a monitor that displays a proposed time or countdown timer to show when an accurate measurement can be taken. By "said first measurement contains a contribution from interferent in the sample" may be meant that the first measurement is at least 1%, for example at least 2%, at least 5% or at least 10% different from the "true" (i.e., actual) concentration of glucose in the sample (as measured, for example, by an electrochemical measurement).

A suitable later time for establishing when the interferent has (at least partially) been metabolised involves carrying out the sequence of steps (i) to (iii) one or more times, each at different time points, until in said step (iii) of comparing said first measurement and said second measurement it is determined that said first measurement contains substantially no or a reduced contribution from the interferent. In other words, one carries one or more measurements, and comparisons, until the interferent has been metabolised to an acceptable extent. By "substantially no or a reduced contribution from interferent" may be meant that the first measurement is at most 10%, preferably at most 5%, more preferably at most 2% and more preferably still at most 1% higher or lower than the "true" (i.e., actual) concentration of glucose in the sample (as measured, for example, by an electrochemical measurement). For example, the method may include carrying out the sequence of steps (i) to (iii) at least twice, at least three times, at least four times or at least five times. In some cases, the method limits the carrying out the sequence of steps (i) to (iii) to no more than twenty times, for example not more than ten times or not more than five times.

In some cases, suitable later time for when the interferent has (at least partially) been metabolised can be established by comparing, in said step (iii), the first measurement and the second measurement and thereby obtaining an estimate of (e.g., calculating) the amount of interferent in the sample at $t_{test}$. The rate of metabolization of many interferents in vivo is a known quantity and therefore the method may then include:

(iv) allowing a sufficient time delay for any interferent present in the sample at $t_{test}$ to substantially clear the sample; and (v) providing incident light to the sensing region of the sensor and detecting the emission of said first fluorophore, thereby obtaining a third measurement of the amount of glucose in the sample, said third measurement having substantially no or a reduced contribution from said interferent.

By allowing "any interferent present in the sample at $t_{test}$ to substantially clear the sample" may be meant that there is sufficient time delay such that the third measurement is at most 10%, preferably at most 5%, more preferably at most 2% and more preferably still at most 1% higher or lower than the "true" (i.e., actual) concentration of glucose in the sample (as measured, for example, by an electrochemical measurement).

As an illustrative example, consider the embodiment in which said interferent is mannitol. The half life, $t_{1/2}$, of mannitol in vivo is approximately 100 minutes and it would be a matter of routine from this for a skilled person to determine, once the amount of mannitol initially present in the sample has been estimated, how long a time delay would be required to bring the concentration of mannitol interferent down to an acceptable level. For example, if after the initial estimate it is established that the amount of mannitol interferent would need to be approximately halved for an acceptable result to be obtained, then one would allow a time delay of approximately 100 minutes. In some cases, a sensor can calculate an estimated time for meeting a certain accuracy and the estimated time can be displayed on a monitor (e.g., as a countdown timer).

Emission Fluorescence as the Second Measurement Method

A method provided herein can include a second measurement method that includes emission fluorescence detection. In some cases, a second measurement can include detecting the emission of a second fluorophore included in a second indicator system including a second receptor for binding to glucose and the second fluorophore. This second indicator system can be included in the sensing region of the glucose sensor that includes the first indicator system.

In some cases, a glucose sensor provided herein can include a first indicator system including a first receptor for binding to glucose and a first fluorophore associated with the first receptor, wherein said first receptor has an association constant $K_{G1}$ with glucose and an association constant $K_{M1}$ with the interferent. This glucose sensor can include a second indicator system including a second receptor for binding to glucose and a second fluorophore associated with the second receptor, wherein said second receptor has an association constant $K_{G2}$ with glucose and an association constant $K_{M2}$ with the interferent, and wherein $K_{G2}/K_{M2}$ is different from $K_{G1}/K_{M1}$.

Methods for measuring the association constant for a particular receptor with a particular guest substance (e.g., glucose or the interferent, for example mannitol) are well known in the art. One such means involves calibrating the changes in fluorescence behaviour (e.g., intensity) of a fluorophore associated with the receptor as the concentration of the guest substance in a control sample containing no other guest substances is varied.

A method provided herein using this glucose sensor can then be carried out by providing incident light to the sensing region of the sensor and obtaining: (a) a first measurement of the amount of glucose by a first measurement method including detecting the emission of said first fluorophore; and (b) a second measurement of the amount of glucose by a second measurement method including detecting the emission of said second fluorophore. The incident light provided to the sensing region can have a suitable wavelength profile to trigger the fluorescence emission of both the first fluorophore and the second fluorophore, i.e. the fluorescence emission of the fluorophores occurs at the same time and can be detected in a single experiment. In some cases, incident light of a first wavelength profile is provided to trigger the fluorescence emission of the first fluorophore and incident light of a second wavelength profile is provided to trigger the fluorescence emission of the second fluorophore with a temporal delay between each wavelength profile, e.g. with a delay of up to ten seconds, for example a delay of up to five seconds.

The second receptor and the second fluorophore are chosen such that $K_{G2}/K_{M2}$ is different from $K_{G1}/K_{M1}$. The second receptor can, for example, be chosen from the receptors described herein as being suitable for the first receptor (e.g., those compounds of formulae (I) and/or (II) described herein). Similarly, the second fluorophore can, for example, be chosen from the fluorophores described herein as being suitable for the first fluorophore. The second indicator system (i.e., the second fluorophore/second receptor system) is different from the first indicator system (i.e., the first fluorophore/first receptor system). In some cases, the second fluorophore is different from the first fluorophore and the second receptor is different from the first receptor. Typically the second receptor is different from the first receptor. Typically both the first receptor and the second receptor have a non-zero association constant with glucose (i.e., both the first receptor and the second receptor are capable of binding to glucose and therefore are sensitive to changes in glucose concentration in the sample).

In some cases, the first fluorophore and second fluorophore are chosen such that their respective peak fluorescence emission wavelengths differ by at least 5 nm, preferably at least 10 nm, more preferably at least 20 nm (when associated with their respective receptors and said receptors are bound to glucose and/or the interferent). A separation of peak fluorescence emission wavelengths can simplify analysis of a fluorescence emission spectrum containing the fluorescence emission of both the first fluorophore and the second fluorophore.

In some cases, when the steps of detecting the emission of the first fluorophore and the second fluorophore, respectively, include detecting the emission lifetime of the first fluorophore and the second fluorophore, respectively, the first and second fluorophores may be chosen such that they have a substantially different fluorescence lifetime (for example, differing by at least 0.5 ns or 1 ns or 2 ns).

The second receptor and the first receptor can have different relative abilities to bind to glucose and the interferent. In some cases, this difference in relative abilities to bind to glucose and the interferent can be significant. For example, it may be preferable that the quotient $[K_{G2}/K_{M2}]/[K_{G1}/K_{M1}]$ is greater than 2 or less than 0.5 (it being appreciated that these values give rise to the same effective difference, depending on whether it is the first or the second receptor that has the higher relative interferent sensitivity). It may be more preferable that the quotient $[K_{G2}/K_{M2}]/[K_{G1}/K_{M1}]$ is greater than 10 or less than 0.1, and even more preferable that the quotient $[K_{G2}/K_{M2}]/[K_{G1}/K_{M1}]$ is greater than 50 or less than 0.02. As the difference in the relative ability of the two receptors to bind to glucose and the interferent increases, a correction for the presence of interferent can become more accurate, even for smaller concentrations of interferent.

In some cases, the two receptors that to bind to glucose and the interferent can have substantially different chemical and/or stereochemical properties. For example, a first receptor and a second receptor can both be boronic acid receptors, but the first receptor can have two boronic acid groups (for example, it is a receptor of the formula (I) or the formula (II) as defined herein) whereas the second receptor can have only one boronic acid group (for example, it is a receptor of the formula (III) as defined herein). A diboronic acid, such as those of formulae (I) or (II) above, may bind to both glucose and a mannitol interferent, whereas a monoboronic acid, such as that of formula (III), may bind more strongly to a mannitol interferent than to glucose.

The second receptor and second fluorophore can be bound to one another and may further be bound to a polymeric matrix such as a hydrogel, or to a dendrimer. Examples of suitable hydrogels and dendrimers are those described in WO 2011/101624, the content of which is incorporated herein by reference. Where a polymeric matrix is used, the particles of polymeric matrix may simultaneously carry the first receptor and first fluorophore together with the second receptor and second fluorophore. In some cases, the second receptor and second fluorophore can be bound to a different polymeric matrix.

Alternatively, the second receptor and second fluorophore may be not directly bonded to one another, for example as described above with reference to the first receptor and first fluorophore.

Comparing the Measurements and Thereby Determining Whether any Interferent is Present in the Sample Methods provided herein can include comparing the first measurement (e.g., the emission of the first fluorophore) and the second measurement (e.g., the emission of the second fluorophore) and thereby determining whether any interferent is present in the sample. Preferably, where it is determined that interferent is present in the sample the method further includes either (a) correcting for the presence of any interferent in the sample, or (b) obtaining a subsidiary measurement of glucose concentration at a later time point when the interferent is (substantially) no longer present in the sample (e.g., when it has been metabolised in vivo). Thus, the step of correcting for the presence of any interferent in the sample or obtaining a subsidiary measurement of glucose concentration can be understood to mean "obtaining a measurement of the amount of glucose in the sample, said measurement having substantially no or a reduced contribution from the interferent", i.e., "quantifying the amount of glucose in the sample".

If the step of "comparing the first measurement and the second measurement" leads to the conclusion that there is (substantially) no interferent in the sample, then one or both of the measurements can be used to determine the glucose concentration without any additional correction or subsidiary measurement step).

The expression "correcting for the presence of any interferent in the sample" takes a broad meaning and includes procedures such as mathematically eliminating the contribution made by the interferent to the first (or second) measurement.

In the context of a method provided herein involving two fluorophores, the skilled person would readily appreciate that because these two fluorophores have different sensitivities to the interferent, comparison of their emission behaviour in a single sample (containing specific glucose and interferent concentrations) can be used to eliminate (by mathematical analysis) the interferent contribution from either measurement and thereby to obtain a correct value for the glucose concentration in the sample. It will be appreciated that implicit in this ability to eliminate the interferent contribution is the ability to calculate the concentrations of both glucose and interferent in the sample.

Some exemplary but non-limiting mathematical equations parameterising the association behaviour of a mixed solution of glucose and interferent in the presence of one or two receptors are presented in the Examples section below. It should be emphasised that these equations are generally applicable to the methods provided herein and are not in any way limited to the specifically described methods and systems (e.g., the particular hydrogels or interferent species) that are used in these Examples.

In certain cases in which the second measurement method includes electrochemically measuring the amount of glucose in the sample, the step of "comparing the first measurement and the second measurement, and thereby determining whether any interferent is present in the sample" can include initially assessing whether the first (fluorescence emission—susceptible to interference from mannitol) and second measurements (electrochemical—not susceptible to interference from interferent) indicate substantially the same glucose concentration. If there is no significant difference, then it will be appreciated that no further steps are required specifically to account for interference (there being no interferent in the sample). However, if there is a significant difference, then the presence of interferent in the sample can be accounted for by carrying out further measurement(s) at later time point(s), i.e. after the interferent has been sufficiently metabolised in vivo, as described elsewhere herein.

Similarly, in certain cases when the second measurement method includes electrochemically measuring the amount of interferent in the sample, the step of "comparing the first measurement and the second measurement, and thereby determining whether any interferent is present in the sample" can include initially assessing whether the second (electrochemical) measurement is indicative of interferent being present in the sample. If not, then it will be appreciated that no further steps are required specifically to account for interference (there being no interferent in the sample). However, if the second measurement does indicate the presence of interferent, then this presence of interferent in the sample can be accounted for by carrying out further measurement(s) at later time point(s), i.e. after the interferent has been sufficiently metabolised in vivo, as described elsewhere herein.

Methods and systems provided herein can includes a first indicator system that is pre-calibrated for detection sensitivity to both glucose and interferent. The second indicator system can also be pre-calibrated if present.

The Glucose Sensor

The present document also provides a glucose sensor. The glucose sensor can be adapted for carrying out the methods provided herein. In some cases, the glucose sensors provided herein can be adapted to carry out a method in which the second measurement method involves detecting fluorescence emission from a second fluorophore, as described herein.

The constituent elements of the glucose sensors provided herein can correspond to those described in the discussion of the methods provided herein above. For example, the sensing region, the first indicator system, the first receptor, the first fluorophore, the second indicator system, the second receptor, the second fluorophore and the optical waveguide, and preferred aspects thereof, are all as herein described with reference to the methods provided herein as discussed above. Since both the first indicator system and the second indicator system are comprised within the sensing region, they are configured such that when contacting the glucose sensor with the sample, both the first indicator system and the second indicator system come into contact with the sample. Thus, typically the sensing region contains a cell or chamber in which both the first and second indicator systems are contained.

The glucose sensor may be an equilibrium glucose sensor.

For the avoidance of doubt, it is emphasised that throughout the present specification, references to a receptor (e.g., the first or second receptor) being "for binding to glucose" means that the receptor is capable of binding to glucose (i.e., has a non-zero association constant with glucose). Consequently the indicator system comprising such a receptor, together with a corresponding fluorophore, is sensitive to the concentration of glucose in the sample.

The Interferent

As used herein, an "interferent" is a substance that is capable of interfering with the binding of glucose to the first receptor comprised in the sensing region of the glucose sensor. Typically, the substance is capable of interfering with the glucose binding by being capable itself of binding to the first receptor (i.e., and thus of competing with glucose for the receptor sites in the glucose sensor). However, other means of interfering can be addressed by the methods and sensors described herein, for example where the substance is capable of interacting with (e.g., binding to) the glucose in such a way as to modify the ability of the glucose to bind to the first receptor.

Typically an interferent that is "capable of interfering with the binding of glucose to the first receptor" is an interferent that has a non-zero association constant with the first receptor (and therefore can compete with glucose for the receptor). For the example, the association constant of the interferent with the first receptor may be at least 1%, or at least 10%, or least 25% of the association constant of glucose with the first receptor.

Typically the interferent is a substance other than protons or hydroxyl ions. Typically the interferent is a substance that is capable of interfering with the binding of glucose to the first receptor comprised in the sensing region of the glucose sensor by a means other than by merely modifying the pH of the sample.

The sample may comprise one interferent or a plurality of different (i.e., chemically different) interferents. Where a plurality of different interferents are present, the methods provided herein can still enable the amount of glucose in the sample to be quantified.

The interferent may be a sugar alcohol or a saccharide other than glucose. Sugar alcohols and saccharides of particular interest include those that may be present in significant quantities in the blood.

The interferent may comprise a cis-diol group. For example, the interferent may be a polyol (e.g., a sugar alcohol or a saccharide) that comprises a cis-diol group. Substances that comprise a cis-diol group are particularly likely to be capable of binding to boronic acid receptors such as the first receptor comprised in the glucose sensors described herein. For the avoidance of doubt, the term "comprise(s) a cis-diol group" does not mean that no hydroxyl groups may be present in the interferent other than those comprised in the cis-diol group. Thus, for example, the interferent may be a polyol (e.g., a sugar alcohol or saccharide) containing at least a cis-diol group and may therefore contain two, three, four, five, six, or even more than six hydroxyl groups in total.

The interferent may be a sugar alcohol or saccharide selected from the group consisting of mannitol, sorbitol, galactitol, inositol, fructose, galactose and arabinose. The interferent may be mannitol.

The interferent may also be an amine, i.e. a compound that contains an amine functional group. The amine functional group may be a primary, secondary or tertiary amine group. Amines of particular interest include those that may be present in significant quantities in the blood. The amine may, for example, be selected from glutamine and catechol amines (e.g., epinephrine, norepinephrine and dopamine).

The interferent may have a molecular weight of less than 1000 daltons, such as less than 500 daltons, or less than 300 daltons, or less than 200 daltons. The present systems and methods may be particularly useful in the context of these low molecular weight interferents, since it may be difficult or impossible to exclude such interferents from the sensing region of the glucose sensor through use of a barrier layer of the type described elsewhere herein.

Methods and sensors provided herein are described below with reference to particular Examples. The invention is not intended to be limited to these particular Examples.

EXAMPLES

The following hydrogels were used in the working Examples:

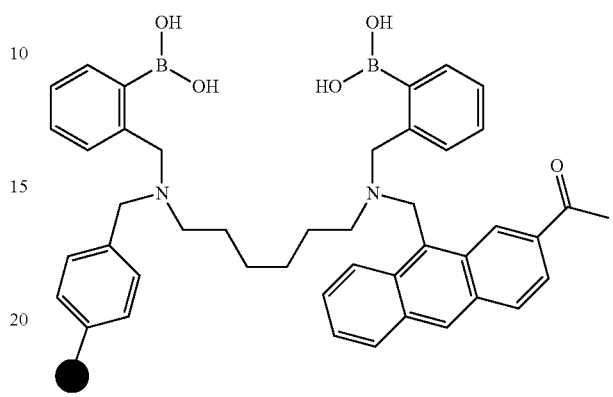

3

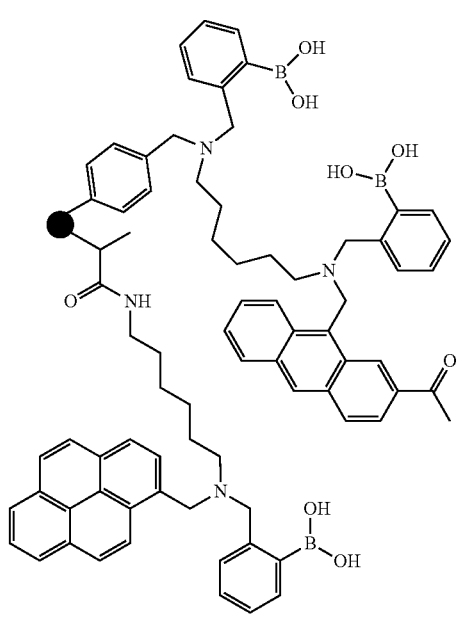

4

● = Hydrogel

Example 1

This Example shows that when a second measurement (for example an electrochemical measurement) is obtained that determines the concentration of a mannitol interferent, the first measurement can be corrected based on that known mannitol concentration to obtain a corrected value of the glucose concentration.

General Equations for Competitive Binding for Two Analytes Using One Receptor

The following equilibria are present when a host, "H", can bind to the analytes D-glucose, "G", and D-mannitol, "M":

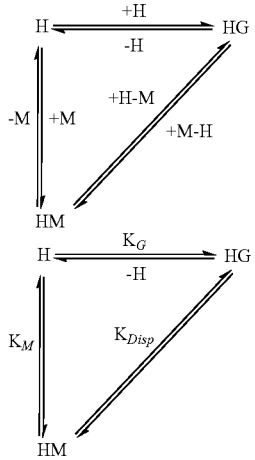

Three equilibria are present:

$$H+G \leftrightarrow HG \quad (1)$$

$$H+M \leftrightarrow HM \quad (2)$$

$$HG+M \leftrightarrow HM+G \quad (3),$$

leading to three association constants:

$$K_G = \frac{[HG]}{[H][G]} \quad (4)$$

$$K_M = \frac{[HM]}{[H][M]} \quad (5)$$

$$K_{Disp} = \frac{[HM][G]}{[HG][M]} = \frac{K_M}{K_G}. \quad (6)$$

From mass balance, it is also known that $$[G]=[G]_i-[HG] \quad (7)$$

$$[M]=[M]_i-[HM] \quad (8)$$

$$[H]=[H]_i-[HG]-[HM] \quad (9),$$

where [X]=equilibrium concentration and $[X]_i$=initial concentration.

Substituting (7) and (9) into (4) gives $$K_G = \frac{[HG]}{[[G]_i - [HG]][[H]_i - [HG] - [HM]]} \quad (10)$$

Rearrangement of (10) leads to $$[HG]^2 + \left[[HM] - [G]_i - [H]_i - \frac{1}{K_G}\right][HG] + [G]_i[[H]_i - [HM]] = 0 \quad (11)$$

Assuming that $K_G[H]_i \ll 1$, the squared term is negligible and therefore $$[HG] = \frac{[G]_i[[H]_i - [HM]]}{[G]_i + [H]_i - [HM] + \frac{1}{K_G}} \quad (12)$$

It can also be assumed that [HM] and $[H]_i \ll [G]_i$, and $1/K_g$. Therefore (12) simplifies to $$[HG] = \frac{[G]_i[[H]_i - [HM]]}{[G]_i + \frac{1}{K_G}}, \quad (13)$$

which can be rewritten as $$\frac{[HG]}{[H]_i} = \frac{\left[1 - \frac{[HM]}{[H]_i}\right]K_G[G]_i}{1 + K_G[G]_i} \quad (14)$$

By substituting (8) and (9) into (5) and carrying out the same manipulations one obtains $$\frac{[HM]}{[H]_i} = \frac{\left[1 - \frac{[HG]}{[H]_i}\right]K_M[M]_i}{1 + K_M[M]_i} \quad (15)$$

(14) and (15) can be solved for [HG] and [HM] by writing them in the matrix form $$\begin{bmatrix} 1+K_G[G]_i & K_G[G]_i \\ K_M[M]_i & 1+K_M[M]_i \end{bmatrix} \begin{bmatrix} \frac{[HG]}{[H]_i} \\ \frac{[HM]}{[H]_i} \end{bmatrix} = \begin{bmatrix} K_G[G]_i \\ K_M[M]_i \end{bmatrix} \quad (16)$$

and inverting the matrix:

$$\begin{bmatrix} \frac{[HG]}{[H]_i} \\ \frac{[HM]}{[H]_i} \end{bmatrix} = \frac{1}{\Delta} \begin{bmatrix} 1+K_M[M]_i & -K_G[G]_i \\ -K_M[M]_i & 1+K_G[G]_i \end{bmatrix} \begin{bmatrix} K_G[G]_i \\ K_M[M]_i \end{bmatrix}, \quad (17)$$

where the determinant is $$\Delta = 1 + K_G[G]_i + K_M[M]_i \quad (18)$$

Thus, $$\frac{[HG]}{[H]_i} = \frac{K_G[G]_i}{1 + K_G[G]_i + K_M[M]_i} \quad (19)$$

$$\frac{[HM]}{[H]_i} = \frac{K_M[M]_i}{1 + K_G[G]_i + K_M[M]_i} \quad (20)$$

For intensity measurements $$i = I - I_0 \quad (21)$$

$$\Delta I = I_1(-I_10) \quad (22)$$

$$i = \left[\frac{[HG]}{[H]_i}\right]\Delta I_G + \left[\frac{[HM]}{[H]_i}\right]\Delta I_M \quad (23)$$

Substituting (19) and (20) into (23) gives $$i = \left[\frac{K_G[G]_i}{1 + K_G[G]_i + K_M[M]_i}\right]\Delta I_G + \left[\frac{K_M[M]_i}{1 + K_G[G]_i + K_M[M]_i}\right]\Delta I_M \quad (24)$$

Substituting (21) and (22) into (24) and rearranging leads to $$I = \frac{I_0 + I_{\infty G}K_G[G]_i + I_{\infty M}K_M[M]_i}{1 + K_G[G]_i + K_M[M]_i} \quad (25)$$

Assuming that $I_{\infty G} = I_{\infty M}$ results in a further simplification of (25) to (26), which allows calculation of the intensity of a fluorophore emission when two analytes are present (in this case glucose and mannitol). Rearrangement of (26) leads to (27) and (28) which allow one to determine the concentration of a first analyte if the concentration of the second analyte and the fluorescent response of a sensor are known:

$$I = \frac{I_0 + I_\infty[K_G[G]_i + K_M[M]_i]}{1 + K_G[G]_i + K_M[M]_i} \quad (26)$$

$$[G]_i = \frac{I - I_0 + (I - I_\infty)K_M[M]_i}{K_G(I_\infty - I)} \quad (27)$$

$$[M]_i = \frac{I - I_0 + (I - I_\infty)K_G[G]_i}{K_M(I_\infty - I)} \quad (28)$$

Calibration of Sensor Containing Hydrogel 3 Against D-Mannitol and D-Glucose

Hydrogel 3 was used to demonstrate that a sensor can be calibrated against both D-mannitol and D-glucose. The results of these calibrations are shown below in Table 1.

TABLE 1

Calibration constants for hydrogel 3 vs. D-glucose and D-mannitol.

| [Glc]/mM | I | [Man]/mM | I |
|---|---|---|---|
| 0.00 | 0.9776 | 0.00 | 0.9601 |
| 17.48 | 1.9571 | 11.64 | 1.6330 |
| 34.23 | 2.3871 | 21.85 | 2.0025 |
| $K_G =$ | 0.0346 | $K_M =$ | 0.0274 |
| $I_0 =$ | 0.9776 | $I_0 =$ | 0.9601 |
| $I_\infty =$ | 3.5782 | $I_\infty =$ | 3.7463 |
| Mod$_{5\,mM}\% =$ | 28.2 | Mod$_{5\,mM}\% =$ | 25.9 |

It can be observed from $K_G$ and $K_M$ that the di-boronic acid receptor of hydrogel 3 is more selective for D-glucose than D-mannitol. $I_0$ for both analytes are the same and the differences observed in measuring $I_\infty$ are probably due to error from the calibrations.

Example 2

This Example shows that a glucose sensor incorporating two receptors that have different relative association constants for glucose and mannitol can be used to correct for the presence of mannitol interferent, and therefore obtain accurate glucose concentration measurements, in a sample containing both glucose and mannitol.

General Equations for Competitive Binding for Two Analytes Using Two Receptors

The following equilibria are present when two hosts, "$H_1$" and "$H_2$", can bind to the analytes D-glucose, "G", and D-mannitol, "M".

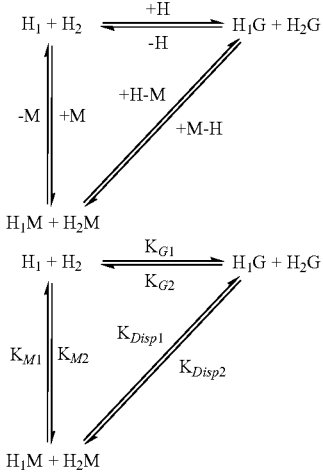

The equilibria present are:

$$H_1 + G \rightleftharpoons H_1G \quad (29)$$

$$H_1 + M \leftrightarrow H_1M \quad (30)$$

$$H_1G + M \leftrightarrow H_1M + G \quad (31)$$

$$H_2 + G \leftrightarrow H_2G \quad (32)$$

$$H_2 + M \rightleftharpoons H_2M \quad (33)$$

$$H_2G + M \rightleftharpoons H_2M + G \quad (34),$$

leading to six association constants:

$$K_{G1} = \frac{[H_1G]}{[H_1][G]} \quad (35)$$

$$K_{M1} = \frac{[H_1M]}{[H_1][M]} \quad (36)$$

$$K_{Disp} = \frac{[H_1M][G]}{[H_1G][M]} = \frac{K_{M1}}{K_{G1}} \quad (37)$$

$$K_{G2} = \frac{[H_2G]}{[H_2][G]} \quad (38)$$

$$K_{M2} = \frac{[H_2M]}{[H_2][M]} \quad (39)$$

$$K_{Disp} = \frac{[H_2M][G]}{[H_2G][M]} = \frac{K_{M2}}{K_{G2}} \quad (40)$$

From mass balance it is also known that:

$$[G]=[G]_i-[H_1G]-[H_2G] \quad (41)$$

$$[M]=[M]_i-[M_1G]-[M_2G] \quad (42)$$

$$[H_1]=[H_1]_i-[H_1G]-[H_1M] \quad (43)$$

$$[H_2]=[H_2]_i-[H_2G]-[H_2M] \quad (44),$$

where [X]=equilibrium concentration and $[X]_i$=initial concentration.

Substituting (41) and (43) into (35) gives $$K_{G1} = \frac{[H_1G]}{[[G]_i - [H_1G] - [H_2G]][[H]_i - [H_1G] - [H_1M]]} \quad (45)$$

Rearrangement of (45) leads to $$[H_1G]^2 + \left[[H_1M] + [H_2G] - [G]_i - [H_1]_i - \frac{1}{K_{G1}}\right] \quad (46)$$
$$[H_1G] + [[H_1]_i - [H_1M]][[G]_i - [H_2G]] = 0$$

Assuming that $K_G[H]_i \ll 1$ means the squared term is negligible and therefore that $$[H_1G] = \frac{[[H_1]_i - [H_1M]][[G]_i - [H_2G]]}{[G]_i + [H_1]_i - [H_1M] - [H_2G] + \frac{1}{K_{G1}}} \quad (47)$$

Since host concentrations are assumed to be extremely small one can also approximate this further by dropping the $[H_2G]$ and $[H_1M]$ terms compared to $[G]_i$ and $1/K_{g1}$ $$[H_1G] = \frac{[G]_i[[H_1]_i - [H_1G]]}{[G]_i + \frac{1}{K_{G1}}}, \quad (48)$$

which can be rewritten as $$\frac{[H_1G]}{[H_1]_i} = \frac{\left[1 - \frac{[H_1M]}{[H_1]_i}\right]K_{G1}[G]_i}{1 + K_{G1}[G]_i} \quad (49)$$

If one substitutes (42) and (43) into (36) and carries out some manipulations one obtains $$\frac{[H_1M]}{[H_1]_i} = \frac{\left[1 - \frac{[H_1G]}{[H_1]_i}\right]K_{M1}[M]_i}{1 + K_{M1}[M]_i} \quad (50)$$

(49) and (50) can be solved for $[H_1G]$ and $[H_1M]$ by writing them in the matrix form $$\begin{bmatrix} 1+K_{G1}[G]_i & K_{G1}[G]_i \\ K_{M1}[M]_i & 1+K_{M1}[M]_i \end{bmatrix} \begin{bmatrix} \frac{[H_1G]}{[H_1]_i} \\ \frac{[H_1M]}{[H_1]_i} \end{bmatrix} = \begin{bmatrix} K_{G1}[G]_i \\ K_{M1}[M]_i \end{bmatrix}, \quad (51)$$

and inverting the matrix $$\begin{bmatrix} \frac{[H_1G]}{[H_1]_i} \\ \frac{[H_1M]}{[H_1]_i} \end{bmatrix} = \frac{1}{\Delta} \begin{bmatrix} 1+K_{M1}[M]_i & -K_{G1}[G]_i \\ -K_{M1}[M]_i & 1+K_{G1}[G]_i \end{bmatrix} \begin{bmatrix} K_{G1}[G]_i \\ K_{M1}[M]_i \end{bmatrix}, \quad (52)$$

where the determinant is $$\Delta = 1 + K_{G1}[G]_i + K_{M1}[M]_1 \quad (53)$$

Thus, $$\frac{[H_1G]}{[H_1]_i} = \frac{K_{G1}[G]_i}{1 + K_{G1}[G]_i + K_{M1}[M]_i} \quad (54)$$

$$\frac{[H_1M]}{[H_1]_i} = \frac{K_{M1}[M]_i}{1 + K_{G1}[G]_i + K_{M1}[M]_i} \quad (55)$$

For the second host, and using the same method and approximations, one obtains $$\frac{[H_2G]}{[H_2]_i} = \frac{K_{G2}[G]_i}{1 + K_{G2}[G]_i + K_{M2}[M]_i} \quad (56)$$

$$\frac{[H_2M]}{[H_2]_i} = \frac{K_{M2}[M]_i}{1 + K_{G2}[G]_i + K_{M2}[M]_i} \quad (57)$$

The light intensities for the two fluorophores can be given by $$i_1 = \left[\frac{[H_1G]}{[H_1]_i}\right]\Delta I_{G1} + \left[\frac{[H_1M]}{[H_1]_i}\right]\Delta I_{M1} \quad (58)$$

$$i_2 = \left[\frac{[H_2G]}{[H_2]_i}\right]\Delta I_{G2} + \left[\frac{[H_2M]}{[H_2]_i}\right]\Delta I_{M2} \quad (59)$$

(54) and (55) can then be substituted into (58) to give $$i_1 = \frac{K_{G1}[G]_i\Delta I_{G1} + K_{M1}[M]_i\Delta I_{M1}}{1 + K_{G1}[G]_i + K_{M1}[M]_i} \quad (60)$$

Expanding and rearranging gives $$t_1 = (\Delta I_{G1} - t_2)K_{G1}[G]_i + (\Delta I_{M1} - t_1)K_{M1}[M]_i \quad (61)$$

Similarly, from substituting (56) and (57) into (59)

$$t_2 = (\Delta I_{G2} - i_2)K_{G2}[G]_i + (\Delta I_{M2} - t_2)K_{M2}[M]_i \quad (62)$$

Writing (61) and (62) in a matrix form and inverting gives $$\begin{bmatrix} [G]_i \\ [M]_i \end{bmatrix} = \frac{1}{\Delta} \begin{bmatrix} (\Delta I_{M2} - i_2)K_{M2} & -(\Delta I_{M1} - i_1)K_{M1} \\ -(\Delta I_{g2} - i_2)K_{G2} & (\Delta I_{G1} - i_1)K_{G1} \end{bmatrix} \begin{bmatrix} i_1 \\ i_2 \end{bmatrix}, \quad (63)$$

where the determinant is $$\Delta = (\Delta I_{G1} - i_1)K_{G1}(\Delta I_{M2} - i_2)K_{M2} - (\Delta I_{G2} - i_2)K_{G2}$$
$$(\Delta I_{M1} - i_1)K_{M1} \quad (64)$$

Thus, $$[G]_i = \frac{(\Delta I_{M2} - i_2)K_{M2}i_1 - (\Delta I_{M1} - i_1)K_{M1}i_2}{(\Delta I_{G1} - i_1)K_{G1}(\Delta I_{M2} - i_2)K_{M2} - (\Delta I_{g2} - i_2)K_{G2}(\Delta I_{M1} - i_1)K_{M1}} \tag{65}$$

Substituting (21) and (22) into (65) gives $$[G]_i = \frac{K_{M2}(I_{\infty M2} - I_2)(I_1 - I_{01}) - K_{M1}(I_{\infty M1} - I_1)(I_2 - I_{02})}{K_{G1}K_{M2}(I_{\infty G1} - I_1)(I_{\infty M2} - I_2) - K_{G2}K_{M1}(I_{\infty g2} - I_2)(I_{\infty M1} - I_1)}, \tag{66}$$

and similarly $$[M]_i = \frac{K_{G1}(I_{\infty G1} - I_1)(I_2 - I_{02}) - K_{G2}(I_{\infty G2} - I_2)(I_1 - I_{01})}{K_{G1}K_{M2}(I_{\infty G1} - I_1)(I_{\infty M2} - I_2) - K_{G2}K_{M1}(I_{\infty g2} - I_2)(I_{\infty M1} - I_1)}. \tag{67}$$

Results Obtained on a Sensor Containing Hydrogel 4 Against D-Mannitol and D-Glucose Two separate boronic acid sensors were immobilised within hydrogel 4. One of these was a di-boronic acid that had similar association constants for both D-glucose and D-mannitol. The second was a mono-boronic acid that was more selective towards D-mannitol. FIG. 7 shows the fluorescent spectra of hydrogel 4 when it was excited at selected wavelengths with increasing D-glucose or D-mannitol concentrations. It is possible to calculate association constants for each of these sensors independently and these results are shown in Table 2 below.

TABLE 2

Association constants for hydrogel 4 to D-glucose and D-mannitol when excited at two differing wavelengths.

| | D-Glucose | | D-Mannitol | |
|---|---|---|---|---|
| | $\lambda_{ex} = 350$ $\lambda_{em} = 380$ | $\lambda_{ex} = 405$ $\lambda_{em} = 487$ | $\lambda_{ex} = 350$ $\lambda_{em} = 380$ | $\lambda_{ex} = 405$ $\lambda_{em} = 487$ |
| $I_0$ | 1.000 | 1.000 | 1.000 | 1.000 |
| $I_\infty$ | 3.915 | 2.725 | 4.077 | 4.699 |
| K/mM$^{-1}$ | 0.005 | 0.020 | 0.063 | 0.009 |

The selectivity of the two boronic acid receptors for D-glucose and D-mannitol are different from each other. The algorithms (66) and (67) can therefore be used to determine both analyte concentrations in a solution containing glucose and mannitol and thus to correct for the presence of mannitol interferent when seeking to obtain an accurate measurement of glucose concentration.

The invention claimed is:

1. A method of determining whether an interferent is present in a glucose-containing sample that may further comprise the interferent and quantifying the amount of glucose, the method comprising:
    (i) providing incident light to a sensing region of a glucose sensor exposed to the glucose-containing sample, wherein the glucose sensor comprises:
        the sensing region comprising at least a first indicator system comprising a first receptor for binding to glucose and a first fluorophore associated with the first receptor; a second indicator system comprising a second receptor for binding to glucose and a second fluorophore associated with the second receptor; a polymeric matrix, wherein the first receptor and first fluorophore and the second receptor and second fluorophore are bound to the polymeric matrix such that the polymeric matrix simultaneously carries the first receptor and first fluorophore together with the second receptor and second fluorophore; and
        an optical waveguide for directing light onto the sensing region;
    (ii) obtaining a first measurement of the amount of glucose by a first measurement method comprising detecting the emission of the first fluorophore;
    (iii) obtaining a second measurement of the amount of glucose by a second measurement method comprising detecting the emission of the second fluorophore, wherein the second measurement method differs in its sensitivity to the amount of the interferent in the sample from the first measurement method; and
    (iv) comparing the first measurement and the second measurement and thereby determining whether any of the interferent is present in the sample;
    wherein the interferent is a substance that is capable of interfering with the binding of glucose to the first receptor,
    wherein once the interferent is determined to be present in the glucose-containing sample, the method further comprising:
    (v) allowing a sufficient time delay for any of the interferent present in the glucose-containing sample to substantially clear the sample; and
    (vi) providing incident light to the sensing region of the glucose sensor and detecting the emission of the first fluorophore, thereby obtaining a third measurement of the amount of glucose in the sample, the third measurement having substantially no or a reduced contribution from the interferent.

2. The method according to claim 1, wherein the first receptor has an association constant $K_{G1}$ with glucose and an association constant $K_{M1}$ with the interferent, and
    wherein the second receptor has an association constant $K_{G2}$ with glucose and an association constant $K_{M2}$ with the interferent, and wherein $K_{G2}/K_{M2}$ is different from $K_{G1}/K_{M1}$.

3. The method according to claim 1, wherein the first measurement and the second measurement are obtained in a single emission detection step.

4. The method according to claim 1, wherein the first fluorophore and the second fluorophore have peak emission wavelengths that differ by at least 5 nm.

5. The method according to claim 2, wherein $[K_{G2}/K_{M2}]/[K_{G1}/K_{M1}]$ is greater than 2 or less than 0.5.

6. The method according to claim 2, wherein the first receptor and the second receptor are boronic acid receptors.

7. The method according to claim 6, wherein the first receptor contains two boronic acid groups and said second receptor contains one boronic acid group.

8. The method according to claim 1, wherein the sample that may further comprise an interferent is an in vivo sample.

9. The method according to claim 1, wherein the sample that may further comprise an interferent is an in vivo sample and wherein the method comprises:

(vii) obtaining the first measurement at a time point $t_{test}$;

(viii) obtaining a fourth measurement by a fourth measurement method, wherein the fourth measurement method comprises electrochemically measuring the amount of glucose, or of the interferent, in the sample at the time point $t_{test}$; and (viiii) comparing the first measurement and the fourth measurement, thereby determining whether the first measurement contains a contribution from the interferent in the sample.

10. The method according to claim 9, wherein the method is carried out on a human or animal subject and the sample is an in vivo bodily fluid of the subject, and wherein step (vii) comprises carrying out an in vivo measurement on the bodily fluid at the time $t_{test}$, and wherein step (viii) comprises extracting a portion of the bodily fluid from the subject at the time $t_{test}$ and carrying out an in vitro electrochemical measurement thereon.

11. The method according to claim 9, wherein the method comprises carrying out the sequence of steps (vii) to (viiii) one or more times, each at different time points, until in the step (viiii) of comparing the first measurement and the second measurement it is determined that the first measurement contains substantially no or a reduced contribution from the interferent.

12. The method according to claim 9, wherein in the step (viiii) of comparing the first measurement and the fourth measurement an estimate of the amount of the interferent in the sample at the time point $t_{test}$ is obtained and wherein the method further comprises:

(iv) allowing a sufficient time delay for any of the interferent present in the sample at test to substantially clear the sample; and (v) providing incident light to the sensing region of the sensor and detecting the emission of the first fluorophore, thereby obtaining a fifth measurement of the amount of glucose in the sample, the fifth measurement having substantially no or a reduced contribution from the interferent.

13. The method according to claim 1, wherein the interferent is selected from the group consisting of (a) an interferent that comprises a cis-diol group and (b) an amine.

14. The method according to claim 13, wherein the interferent that comprises a cis-diol group is selected from the group consisting of a sugar alcohol and a saccharide.

15. The method according to claim 1, wherein the interferent is selected from the group consisting of mannitol, sorbitol, galactitol, inositol, fructose, galactose, arabinose, glutamine and catechol amines.

16. A glucose sensor for quantifying and performing the method of claim 2, wherein said first receptor has an association constant Km with glucose and an association constant KM1 with said interferent, and wherein said second receptor has an association constant $K_{G2}$ with glucose and an association constant $K_{M2}$ with said interferent, and wherein $K_{G2}/K_{M2}$ is different from $K_{G1}/K_{M1}$.

17. The method according to claim 1, wherein the method further comprises calculating the concentration of glucose in the sample.

18. The method according to claim 1, wherein the method further comprises correcting for the presence of any of the interferent in the sample.

19. The method according to claim 1, wherein the first receptor and second receptor are boronic acid receptors or comprise one or more groups of formula $H_3AsO_3$, $H_2AsO_3$—, $H_6TeO_6$, $H_5TeO_6$—, $Ge(OH)_6$ or $GeO(OH)_3$—, or derivatives thereof.

* * * * *